United States Patent
Takahashi et al.

(10) Patent No.: US 10,885,037 B2
(45) Date of Patent: Jan. 5, 2021

(54) DETECTION METHOD, DETECTION APPARATUS, AND NON-TRANSITORY COMPUTER-READABLE STORAGE MEDIUM

(71) Applicant: FUJITSU LIMITED, Kawasaki (JP)

(72) Inventors: Hidekazu Takahashi, Kawasaki (JP); Shinichiro Tago, Shinagawa (JP); Nobuyuki Igata, Kawasaki (JP)

(73) Assignee: FUJITSU LIMITED, Kawasaki (JP)

( * ) Notice: Subject to any disclaimer, the term of this patent is extended or adjusted under 35 U.S.C. 154(b) by 96 days.

(21) Appl. No.: 16/049,881

(22) Filed: Jul. 31, 2018

(65) Prior Publication Data

US 2019/0042625 A1 Feb. 7, 2019

(30) Foreign Application Priority Data

Aug. 2, 2017 (JP) .................. 2017-150277

(51) Int. Cl.
| | |
|---|---|
| *G06F 7/00* | (2006.01) |
| *G06F 17/00* | (2019.01) |
| *G06F 16/2455* | (2019.01) |
| *A61B 5/00* | (2006.01) |
| *G06F 16/28* | (2019.01) |
| *G06F 16/23* | (2019.01) |
| *G06F 16/906* | (2019.01) |

(Continued)

(52) U.S. Cl.
CPC ...... *G06F 16/24564* (2019.01); *A61B 5/7264* (2013.01); *G06F 16/2365* (2019.01); *G06F 16/285* (2019.01); *G06F 16/906* (2019.01); *G16H 50/20* (2018.01); *G16H 50/70* (2018.01); *A61B 5/7282* (2013.01)

(58) Field of Classification Search
CPC .... G06F 16/2246; G06F 16/245; G06F 16/31; G06F 17/18; G06F 16/38; G06F 16/93
See application file for complete search history.

(56) References Cited

U.S. PATENT DOCUMENTS

2007/0015911 A1* 1/2007 Warder ............... C07K 1/30
530/414
2011/0301221 A1* 12/2011 Lin .................... C12Q 1/6886
514/44 A (Continued)

FOREIGN PATENT DOCUMENTS

| JP | H02-204835 A | 8/1990 |
|---|---|---|
| JP | H08-95788 A | 4/1996 |
| JP | H10-275085 A | 10/1998 |

*Primary Examiner* — Tuan A Pham
(74) *Attorney, Agent, or Firm* — Fujitsu Patent Center

(57) ABSTRACT

A detection method includes: executing first processing that includes determining whether or not at least any of one or more attribute values included in an input class corresponds to any of one or more conditions defined in a subject class; executing second processing that includes determining whether or not at least any of the one or more attribute values included in the input class corresponds to a negation class including one or more second conditions that contradict the one or more conditions defined in the subject class; and executing third processing that includes outputting information relating to the input class determined as non-corresponding by the second processing when both a determination result in the first processing and a determination result in the second processing are non-corresponding.

15 Claims, 19 Drawing Sheets

(51) Int. Cl.
*G16H 50/20* (2018.01)
*G16H 50/70* (2018.01)

(56) References Cited

U.S. PATENT DOCUMENTS

| | | | |
|---|---|---|---|
| 2012/0220471 A1* | 8/2012 | Gomez Rivas | G01N 21/6428 506/7 |
| 2013/0288250 A1* | 10/2013 | Chibon | C12Q 1/6886 435/6.11 |
| 2015/0191790 A1* | 7/2015 | Modiano | C12Q 1/6886 424/94.6 |
| 2016/0333100 A1* | 11/2016 | Lee | G01N 33/6872 |
| 2017/0105997 A1* | 4/2017 | Creasy | A61K 45/06 |

* cited by examiner

FIG. 5

```
                                                  ┌ 122
┌─────────────────────────────────────┐
│ · INFERENCE TARGET CLASS LIST       │
│   ={"¬C and ¬D"}                    │
│ · EXCLUDED CLASS LIST               │
│   ={"A or B", "¬A and ¬B"}          │
│ · UNCERTAIN BASIC CLASS LIST        │
│   ={C, D}                           │
└─────────────────────────────────────┘
```

FIG. 7

| PATIENT ID | AGE | SEX | DISEASE NAME 1 | DISEASE NAME 2 | ... | SBP VALUE | ... | NUMBNESS | DIZZINESS | ... |
|---|---|---|---|---|---|---|---|---|---|---|
| OB1010 | 55 | FEMALE | LACUNAR INFARCTION | HYPERTENSION | ... | UNKNOWN | ... | UNKNOWN | UNKNOWN | ... |
| OB1011 | 62 | MALE | ACUTE CEREBRAL INFARCTION | — | ... | 190 | ... | PRESENT | ABSENT | ... |
| ... | ... | ... | ... | ... | ... | ... | ... | ... | ... | ... |

FIG. 15

PLEASE CHECK FOLLOWING POINT ABOUT PATIENT ID: OB1010

- ○ NUMBNESS IS PRESENT
- ○ DIZZINESS IS PRESENT
- ○ BOTH NUMBNESS AND DIZZINESS ARE ABSENT

ENTER 8100
8101
8111

DETECTION METHOD, DETECTION APPARATUS, AND NON-TRANSITORY COMPUTER-READABLE STORAGE MEDIUM

CROSS-REFERENCE TO RELATED APPLICATION

This application is based upon and claims the benefit of priority of the prior Japanese Patent Application No. 2017-150277, filed on Aug. 2, 2017, the entire contents of which are incorporated herein by reference.

FIELD

The embodiments discussed herein are related to a detection method, a detection apparatus, and a non-transitory computer-readable storage medium.

BACKGROUND

There is an expert system that causes a computer to carry out implementation by a specialist by deriving a result from acquired information with use of a knowledge base and an inference mechanism. For example, there is a technique using three logical values defined by adding "unknown" to "true" and "false" that are logical values of a limiting condition, for example.

Furthermore, in object-oriented techniques in which knowledge (processing) for identifying a certain diagnostic result is encapsulated in units of object, there is also the following technique. When a new object is generated from a given class definition, information on a certain diagnostic target is set as an attribute value of the object. Thereby, which diagnostic result among assumed diagnostic results defined in advance the information corresponds to is identified from the attributed value of the object. Moreover, there is the following technique. The respective terms of a conjunctive normal form created by simplification from given plural pieces of data are extracted as a concept for classifying data and each piece of data is classified with permission of overlapping regarding each piece of data that satisfies a respective one of the extracted items. In this technique, the respective concept classes each corresponding to the concept of a respective one of the items are created and a concept hierarchy is created.

Examples of the related art include Japanese Laid-open Patent Publication No. 02-204835, Japanese Laid-open Patent Publication No. 08-095788, and Japanese Laid-open Patent Publication No. 10-275085.

SUMMARY

According to an aspect of the embodiments, a detection method includes: executing first processing that includes determining whether or not at least any of one or more attribute values included in an input class corresponds to any of one or more conditions defined in a subject class; executing second processing that includes determining whether or not at least any of the one or more attribute values included in the input class corresponds to a negation class including one or more second conditions that contradict the one or more conditions defined in the subject class; and executing third processing that includes outputting information relating to the input class determined as non-corresponding by the second processing when both a determination result in the first processing and a determination result in the second processing are non-corresponding.

The object and advantages of the invention will be realized and attained by means of the elements and combinations particularly pointed out in the claims.

It is to be understood that both the foregoing general description and the following detailed description are exemplary and explanatory and are not restrictive of the invention, as claimed.

BRIEF DESCRIPTION OF DRAWINGS

FIG. 5 illustrates one example of a class list in embodiment 1;
FIG. 7 illustrates one example of patient master data in embodiment 1;
FIG. 15 illustrates one example of an inference result screen in embodiment 1.

DESCRIPTION OF EMBODIMENTS

Detection of a diagnostic result (diagnostic result may be referred to as detection subject class or subject class) to which information on a certain diagnostic target (diagnostic target may be referred to as input class) corresponds is tried. If part of the information on the diagnostic target is "uncertain," the information corresponds to none of assumed diagnostic results defined in advance and "non-corresponding" is possibly output as the diagnostic result. However, if "non-corresponding" is output as the diagnostic result, it is difficult to discern whether or not part or all of the information on the diagnostic target is "uncertain." For example, the execution result is similarly "non-corresponding" in both the case in which at least part of the information on the diagnostic target is "uncertain" and thus the information corresponds to none of the diagnostic results and the case in which a valid value set in the information on the diagnostic target corresponds to none of the diagnostic results. As a result, it is difficult to identify which part of the information on the diagnostic target is undefined, for example.

In one aspect of the present disclosure, providing a detection method, a detection apparatus, and a recording medium that may support proper classification of the input class is intended.

Embodiments of a detection method, a detection apparatus, and a recording medium disclosed by the present application will be described in detail below based on the drawings. The present disclosure is not limited by these embodiments. Furthermore, the respective embodiments represented below may be combined as appropriate in a range in which contradiction is not caused. In the embodiment below, the same part as a part represented in a drawing explained earlier is given the same numeral and overlapping description is omitted.

Embodiment 1

Figure 1:
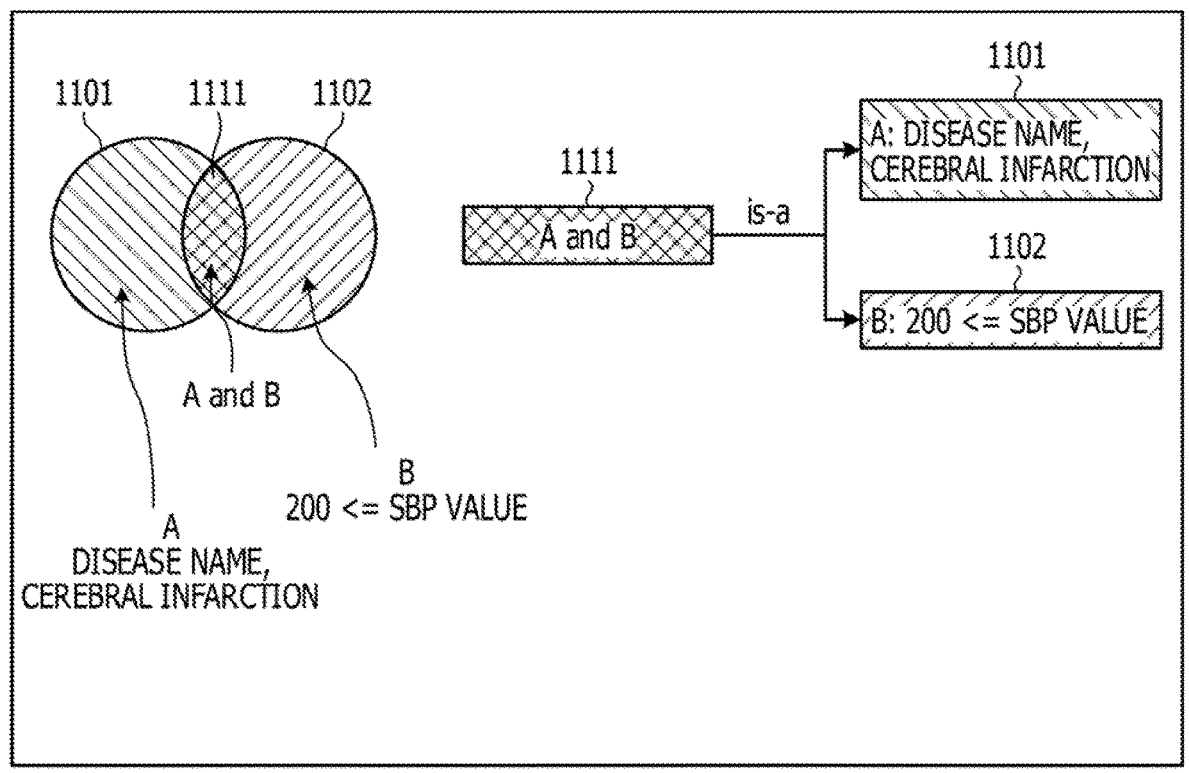
FIG. 1 illustrates one example of a subject class.

A detection apparatus 100 in the present embodiment may be used for the purpose of executing inference processing of an input class (input class may be referred to as input object, input information, diagnostic target, and so forth) and outputting the result of the inference processing based on a medical care guideline or the like, for example. The medical care guideline is a guideline made by marshalling the latest information by a specialist regarding the evidence and procedure of medical care such as prevention, diagnosis, treatment, and prognostic estimation of disease for the purpose of supporting proper diagnosis and treatment in medical sites. The medical care guideline in the present embodiment includes combinations of diagnostic conditions described in text and medicines recommended to be prescribed and coping methods such as improvement in the lifestyle in the case in which the result of inference processing accords with the diagnostic condition, for example. The detection apparatus 100 in the present embodiment executes inference processing of an input class with respect to a subject class (subject class may be referred to as category) like one illustrated in FIG. 1, for example, and outputs a coping method or the like that accords with the result of the inference processing. FIG. 1 is a diagram illustrating one example of a subject class. FIG. 1 illustrates one example of the subject class in the case of inferring cases (cases may be referred to as diagnostic result, subject class, category, and so forth) corresponding to information on a patient (patient may be referred to as diagnostic target, input class, input object, and so forth) by using the detection apparatus 100 in the present embodiment.

In the present embodiment, the subject class may be generated by carrying out a logical connection of individual conditions as single concepts included in a diagnostic condition or the like represented in the medical care guideline or the like. For example, the subject class may include one or more conditions (condition may be referred to as diagnostic condition, individual condition, determination condition, classification condition, and so forth) that may be used when an input class is classified into a certain category. The input class may include one or more attribute values (attribute value may be referred to as attribute, condition, and so forth). For example, FIG. 1 illustrates one example of a subject class generated based on a diagnostic condition described in text of "the disease name is cerebral infarction and the SBP value is 200 or larger." If determining that an input class accords with the subject class illustrated in FIG. 1, for example, the detection apparatus 100 in the present embodiment outputs prescription medicine, coping method, and so forth corresponding to the diagnostic condition of "the disease name is cerebral infarction and the SBP value is 200 or larger." Furthermore, in the following, the single concept that is an individual condition included in a diagnostic condition and is difficult to further segment will be represented as "basic class" in some cases.

A subject class 1111 illustrated in FIG. 1 is represented based on an AND connection of a basic class 1101 of "the disease name is cerebral infarction" and a basic class 1102 of "the SBP value is 200 or larger." For example, when the basic class 1101 is expressed as "A" and the basic class 1102 is expressed as "B," the subject class 1111 is represented by a logical expression of "A and B." In the following, each basic class is represented by an English capital letter such as "A."

The subject class 1111 illustrated in FIG. 1 becomes "corresponding" If an input class corresponds to both the basic class 1101 of "A: disease name, cerebral infarction" and the basic class 1102 of "B: 200<=SBP value" (is in "is-a" relationship). For example, the subject class 1111 becomes "non-corresponding" if the input class does not correspond to either one of the basic classes 1101 and 1102. Here, determination of the correspondence of the input class to the subject class may be carried out by comparing each of one or more attributes possessed by the input class with one or more basic classes possessed by the subject class.

Figure 2A:
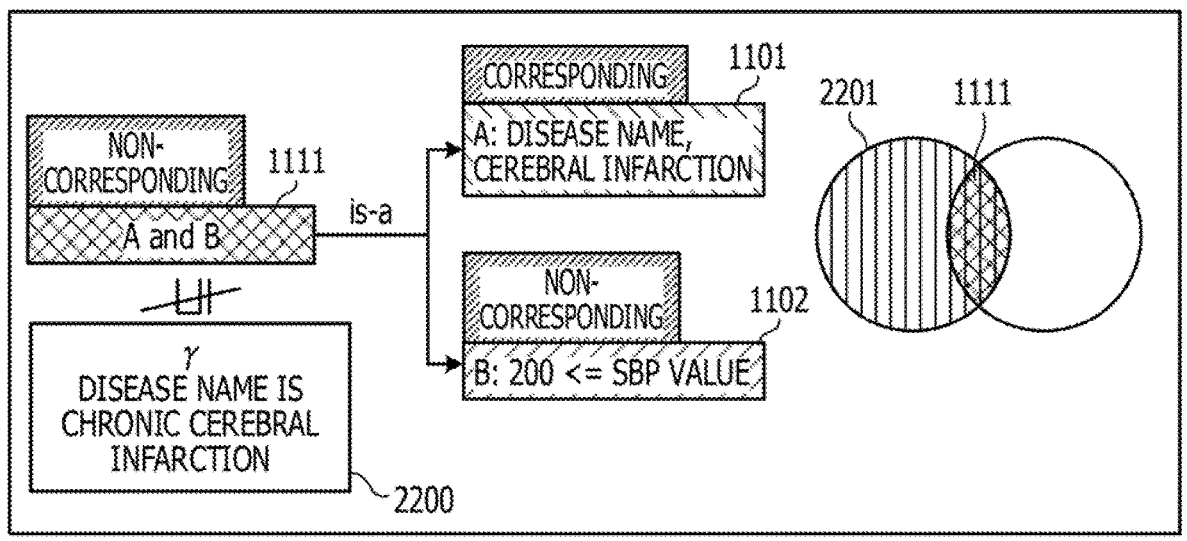
FIG. 2A illustrates one example of a case in which an input class does not correspond to a subject class.

Incidentally, among the cases in which the output result is "non-corresponding" are the case in which at least part of conditions (condition may be referred to as attribute, attribute value, and so forth) included in the input class is uncertain and whether or not this part corresponds to any basic class is unknown and the case in which a condition (condition may be referred to as attribute, attribute value, and so forth) included in the input class corresponds to the negation of any basic class. FIG. 2A is a diagram illustrating one example of a case in which an input class does not correspond to a subject class. FIG. 2A represents an inference result (this inference result may be referred to as first inference result, first determination result, and so forth) when an input class 2200 is "the disease name is chronic cerebral infarction" and the test result of the SBP value is unknown.

In the example illustrated in FIG. 2A, the input class 2200 has an attribute value "chronic cerebral infarction" regarding an attribute "disease name." Suppose that it is determined that the attribute value "chronic cerebral infarction" of the attribute "disease name" possessed by the input class 2200 is included in "cerebral infarction" based on disease name master data 123 to be described later. For this reason, it is inferred that the input class 2200 is "corresponding" to basic class A (1101) (condition: disease name=cerebral infarction). On the other hand, the attribute value of an attribute "SBP value" of the input class 2200 is uncertain (uncertain attribute value may be referred to as null value). For this reason, the input class 2200 is determined as "non-corresponding" regarding basic class B (1102) (condition: SBP value≥200). In a Venn diagram illustrated in FIG. 2A, the input class 2200 is in the state in which it is uncertain whether or not an inference result 2201 (range represented by vertical lines) of the input class 2200 is included in the range 1111 equivalent to the logical expression "A and B"

(range in which oblique lines cross). As a result, it is inferred that the input class 2200 exemplified in FIG. 2A is "non-corresponding" regarding the subject class 1111.

Figure 2B:
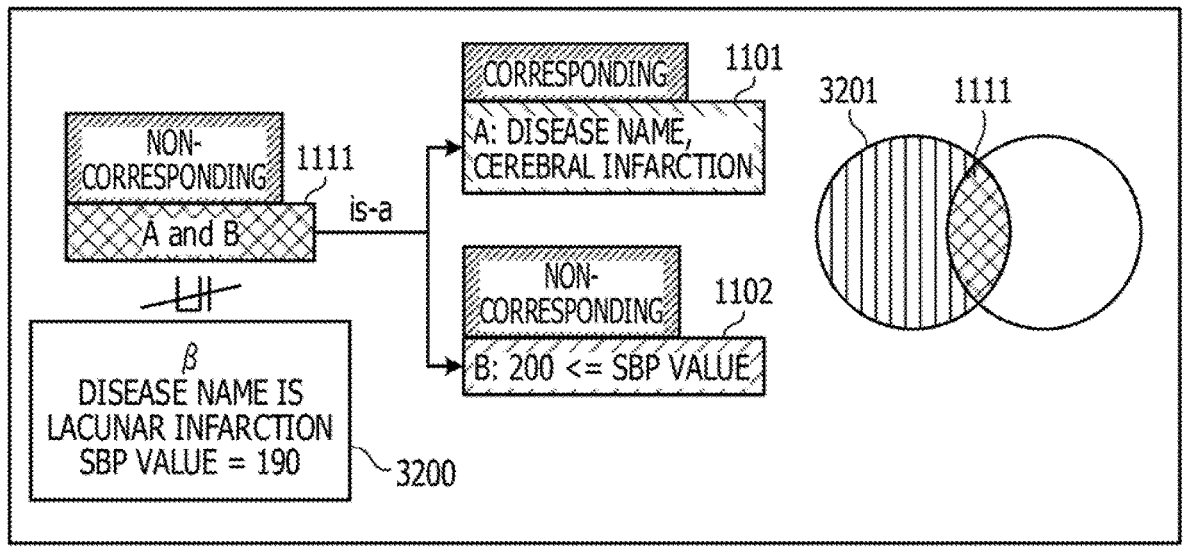
FIG. 2B illustrates another example of a case in which an input class does not correspond to a subject class.

Next, FIG. 2B is a diagram illustrating another example of a case in which an input class does not correspond to a subject class. FIG. 2B represents an inference result (this inference result may be referred to as first inference result, first determination result, and so forth) when an input class 3200 is "the disease name is lacunar infarction and the test result of the SBP value is 190."

In the example illustrated in FIG. 2B, the input class 3200 has an attribute value "lacunar infarction" regarding the attribute "disease name." Suppose that, also in this case, it is determined that the attribute value "lacunar infarction" of the attribute "disease name" possessed by the input class 3200 is included in "cerebral infarction" based on the disease name master data 123. For this reason, it is inferred that the input class 3200 is "corresponding" to basic class A (1101) (condition: disease name=cerebral infarction). On the other hand, the attribute value "190" of the attribute "SBP value" of the input class 3200 is determined as "non-corresponding" regarding basic class B (1102) (condition: SBP value≥200). In a Venn diagram illustrated in FIG. 2B, an inference result 3201 (range represented by vertical lines) of the input class 3200 is not included in the range 1111 equivalent to the logical expression "A and B" (range in which oblique lines cross). As a result, it is inferred that the input class 3200 exemplified in FIG. 2B is also "non-corresponding" regarding the subject class 1111.

In the examples described above, both the input classes 2200 and 3200 are determined as "non-corresponding" with respect to the subject class 1111. However, whether or not an attribute value (condition) of the input class is in the uncertain state is unknown. Furthermore, in the above examples, in the case in which part of the attribute values (conditions) in the input class is in the uncertain state, it is difficult to discern which attribute (condition) is uncertain from the determination result of "non-corresponding" to the subject class 1111. For example, it is difficult to discern which attribute to regard as the identification target of the attribute value in order to definitely determine whether or not the input class corresponds to any subject class 1111. For example, the inference result 2201 of the input class 2200 exemplified in FIG. 2A has room for corresponding to the subject class 1111. On the other hand, it is certain that the inference result 3201 of the input class 3200 exemplified in FIG. 2B does not correspond to the subject class 1111. However, in the examples described above, only that the output result is "non-corresponding" is indicated regarding both input classes and whether or not an attribute value (condition) of the input class is in the uncertain state is unknown. Here, the output result about whether or not the input class corresponds to the subject class may be referred to as first inference result, first determination result, first output result, and so forth.

In the present embodiment, determination of whether or not the input class corresponds is carried out also regarding the "negation class" of the subject class 1111. The negation class "!R" in the present embodiment is generated by carrying out a logical connection of the classes that contradict the basic classes included in the subject class. For example, the negation class "!R" of the subject class 1111, which is "A and B," is "!A or !B." In the following, a class that contradicts class X will be expressed as "!X" or "¬ X" in some cases. Furthermore, in the following, the negation class of the subject class will be represented simply as the "negation class" in some cases. If the input class is "non-corresponding" regarding all subject classes 1111, determination of whether or not the input class corresponds to the "negation class" of the subject class 1111 may be carried out. For example, the determination target of whether or not the target corresponds to the "negation class" of the subject class 1111 may be limited to the input class determined as "non-corresponding" regarding all subject classes 1111.

Figure 3A:
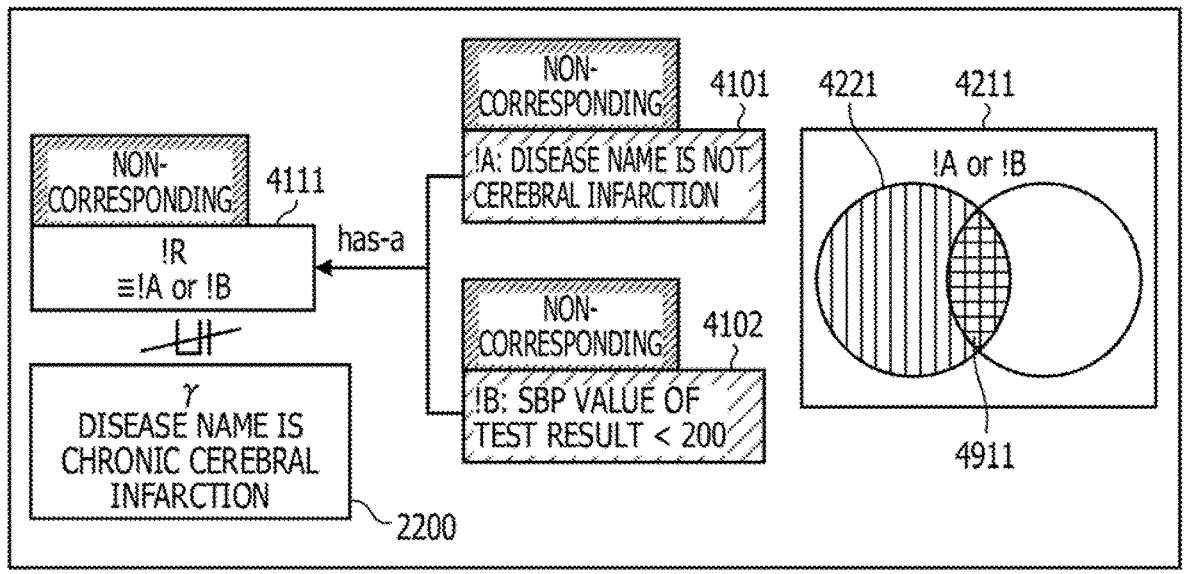
FIG. 3A illustrates one example of a negation class of a subject class in embodiment 1.

FIG. 3A is a diagram illustrating one example of a negation class of a subject class in embodiment 1. As illustrated in FIG. 3A, a negation class 4111 is generated based on an OR connection 4211 of a basic class 4101 "!A: disease name is not cerebral infarction" that contradicts basic class A (1101) and a basic class 4102 "!B: SBP value<200" that contradicts basic class B (1102). For example, the negation class 4111 illustrated in FIG. 3A becomes "corresponding" if the input class corresponds to at least either the basic class 4101 or the basic class 4102 (is in "has-a" relationship) (if the input class does not correspond to a range 4911 represented by horizontal lines).

In the input class 2200 exemplified in FIG. 3A, similarly to FIG. 2A, the attribute value of the attribute "disease name" is "chronic cerebral infarction" and the attribute value of the attribute "SBP value" is in the uncertain state. Suppose that, similarly to FIG. 2A, it is determined that the attribute value "chronic cerebral infarction" of the attribute "disease name" possessed by the input class 2200 is included in "cerebral infarction" based on the disease name master data 123 to be described later. For this reason, it is determined that the input class 2200 does not correspond to the basic class 4101 (condition: disease name≠ cerebral infarction) included in the negation class 4111, and the input class 2200 is determined as "non-corresponding" also regarding the basic class 4102 (condition: SBP value<200). In this case, regarding the input class 2200, the output result with respect to the negation class 4111 (output result may be referred to as second inference result, second determination result, second output result, and so forth) is "non-corresponding."

Figure 3B:
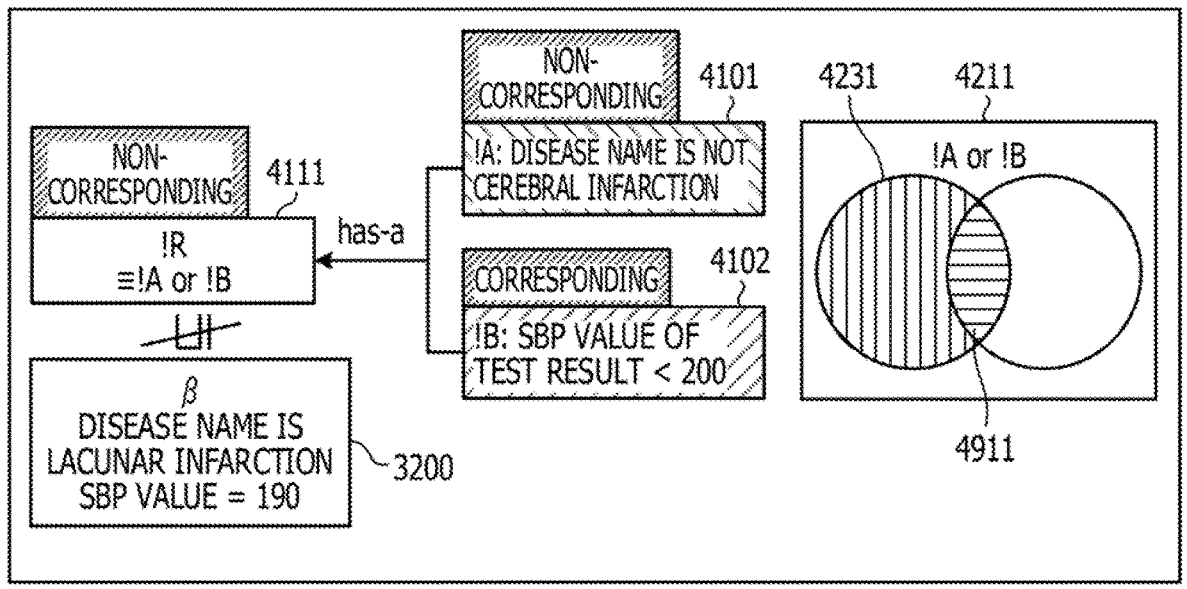
FIG. 3B illustrates another example of a negation class of a subject class in embodiment 1.

On the other hand, FIG. 3B is a diagram illustrating another example of the negation class of the subject class in embodiment 1. In the input class 3200 exemplified in FIG. 3B, similarly to FIG. 2B, the attribute value of the attribute "disease name" is "lacunar infarction" and the attribute value of the attribute "SBP value" is "190." Suppose that, similarly to FIG. 2B, it is determined that the attribute value "lacunar infarction" of the attribute "disease name" possessed by the input class 3200 is included in "cerebral infarction" based on the disease name master data 123 to be described later. As illustrated in FIG. 3B, it is determined that the input class 3200 does not correspond to the basic class 4101 (condition: disease name≠ cerebral infarction), but the input class 3200 is determined as "corresponding" regarding the basic class 4102 (condition: SBP value<200). In this case, regarding the input class 3200, the output result with respect to the negation class 4111 (output result may be referred to as second inference result, second determination result, and so forth) is "corresponding."

For example, it is uncertain whether or not an inference result 4221 (range represented by vertical lines) of the input class 2200 corresponds to the range 4911, which is not included in the OR connection 4211, as illustrated in FIG. 3A. In this case, the input class 2200 is determined as "non-corresponding" to the negation class 4111. On the other hand, an inference result 4231 (range represented by vertical lines) of the input class 3200 does not correspond to the range 4911, which is not included in the OR connection 4211, as illustrated in FIG. 3B. For this reason, the input class 3200 is determined as "corresponding" to the negation class 4111. For example, in the present embodiment, the input classes 2200 and 3200, which are both "non-corresponding" regarding the subject class 1111, are "non-corresponding" and "corresponding" regarding the negation class 4111. Thus, the inference result differs. For example, the output result indicating that the input class is "non-corresponding" to the negation class implies that part of the conditions of the input class is uncertain. On the other hand, the output result indicating that the input class is "corresponding" to the negation class implies that the input class has been negated with respect to the subject class. This makes it possible to discern whether part of the conditions of the input class is uncertain or the input class has been negated in the case in which the result indicating that the input class is "non-corresponding" to the subject class is output. For example, regarding the input class 3200, it may be identified that the input class has been negated. Regarding the input class 2200, it may be identified that part of the conditions in the input class is uncertain. Here, the output result of whether or not the input class corresponds to the negation class may be referred to as second inference result, second determination result, second output result, and so forth. For example, a doctor who has confirmed the first inference result and the second inference result may discern which input class has an uncertain item (attribute). This allows the doctor to know which subject class the input class corresponds to by identifying the value of the item (attribute) about the input class having the uncertain item (attribute). Such operation is useful in supporting proper classification of the input class.

Moreover, if the input class is "non-corresponding" to both the subject class and the negation class, the detection apparatus 100 in the present embodiment may repeat inference processing regarding lower-level classes of each class. Here, it shall be noted that the subject classes may be defined as individual elements in a knowledge base having a hierarchical structure. This applies also to the negation classes. In the example illustrated in FIG. 2A, because the input class 2200 is "non-corresponding" to the subject class 1111, the detection apparatus 100 may repeat inference processing of the input class with respect to the basic classes 1101 and 1102, which are lower-level classes of the subject class 1111. For example, if the first inference result relating to the correspondence of the input class to the subject class is "non-corresponding," the detection apparatus 100 may employ each of one or more basic classes included in the subject class as a new subject class and determine the correspondence of the input class. At this time, the detection apparatus 100 may repeat inference processing of the input class also regarding the basic classes 4101 and 4102, which are lower-level classes of the negation class 4111 that is illustrated in FIG. 3A and corresponds to the subject class 1111. For example, if the second inference result relating to the correspondence of the input class to the negation class is "non-corresponding," the detection apparatus 100 may employ each of one or more basic classes included in the negation class as a new negation class and determine the correspondence of the input class.

In the example illustrated in FIG. 2A, the detection apparatus 100 determines that the input class 2200 is "corresponding" to the basic class 1101 and is "non-corresponding" to the basic class 1102. Furthermore, in the example illustrated in FIG. 3A, the detection apparatus 100 determines that the input class 2200 is "non-corresponding" to the basic class 4101 corresponding to the basic class 1101 and is "non-corresponding" also to the basic class 4102 corresponding to the basic class 1102. For example, the input class 2200 is determined as "non-corresponding" both to the basic class 1102, which is a lower-level class of the subject class, and to the basic class 4102, which is a lower-level class of the negation class. In this case, the detection apparatus 100 may output the basic class 1102 and the basic class 4102, which are "non-corresponding" to the input class 2200, as uncertain classes. For example, if the inference result relating to the correspondence of the input class to a lower-level class of the subject class (this inference result may be referred to as third inference result) is "non-corresponding" and the inference result relating to the correspondence of the input class to a lower-level class of the negation class corresponding to this subject class (this inference result may be referred to as fourth inference result) is "non-corresponding," the detection apparatus 100 may output information relating to these lower-level classes as uncertain classes. This makes it possible to discern that the attribute (condition) relating to the basic class 1102 and the basic class 4102, for example, "SBP value," is uncertain and whether or not the input class corresponds to the subject class 1111 may be definitely determined if the SBP value becomes clear.

As described above, if the input class corresponds to neither the subject class nor the negation class, the detection apparatus 100 may output information relating to a basic class that is "non-corresponding" as an uncertain class. This allows the detection apparatus 100 to be utilized for identifying which basic class is a basic class regarding which the relevant attribute (condition) is uncertain. A doctor who has confirmed such an inference result may come to know which item (attribute) in the input class is to be identified for allowing the input class to correspond to the subject class. Such operation is useful in supporting proper classification of the input class.

[Functional Blocks]

Figure 4:
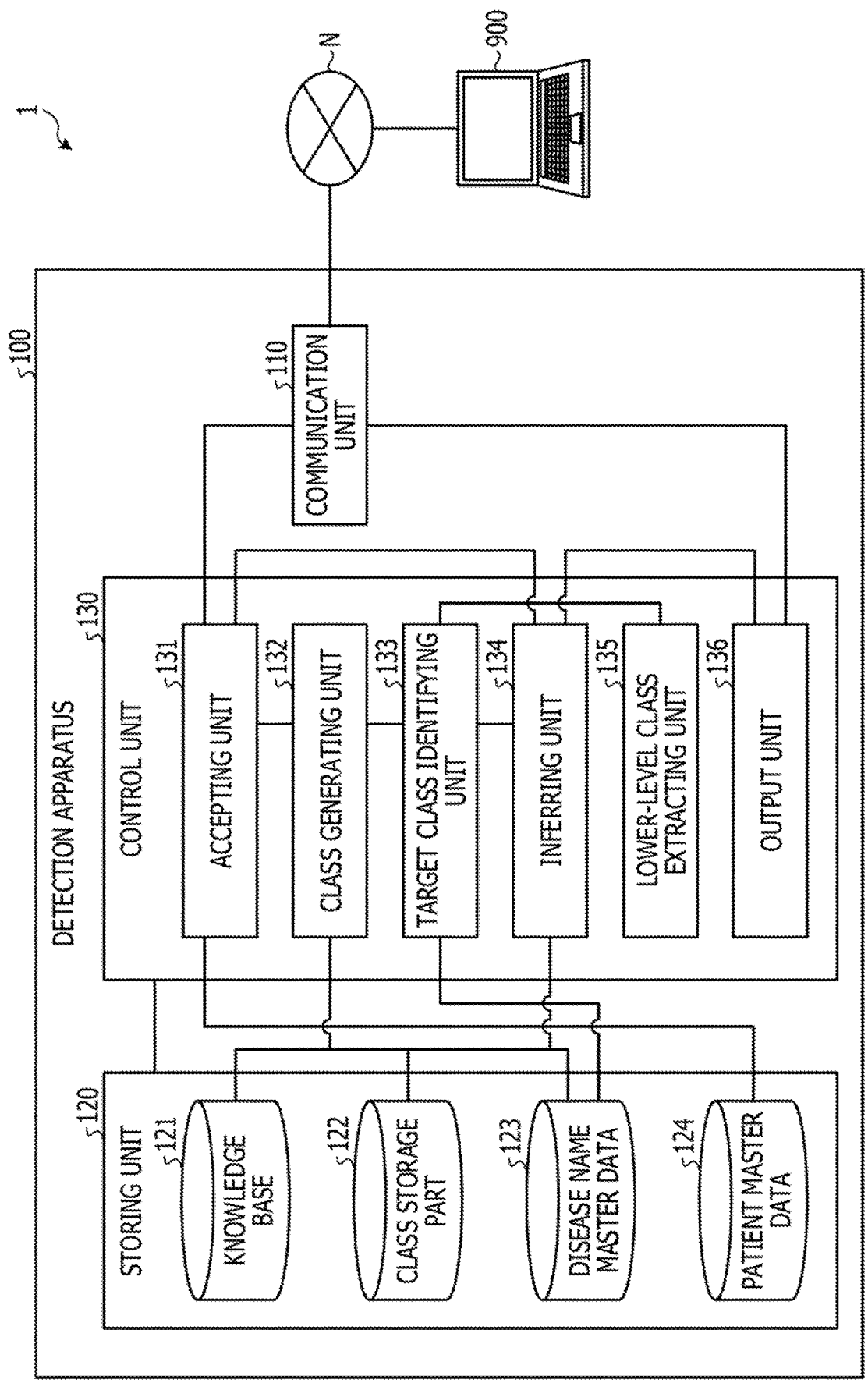
FIG. 4 illustrates one example of a detection system in embodiment 1.

Next, a detection system in the present embodiment will be described by using FIG. 4. FIG. 4 is a diagram illustrating one example of a detection system in embodiment 1. A detection system 1 illustrated in FIG. 4 includes the detection apparatus 100 and a user terminal 900.

In the present embodiment, the detection apparatus 100 and the user terminal 900 are coupled communicably through a wireless or wired network N. The number of user terminals 900 in FIG. 4 is one example and a configuration in which the detection system 1 includes an arbitrary number of user terminals 900 may be employed.

The user terminal 900 illustrated in FIG. 4 is used by a user of detection processing by the detection apparatus 100. The user terminal 900 transmits information input by the user to the detection apparatus 100 and outputs information received from the detection apparatus 100. The user terminal 900 is a portable computer such as a smartphone, tablet, or notebook computer. Besides, the user terminal 900 may be a stationary computer or the like.

The detection apparatus 100 in the present embodiment includes a communication unit 110, a storing unit 120, and a control unit 130 as illustrated in FIG. 4. The detection apparatus 100 in the present embodiment is a computer such as a server computer that accepts a processing request from the user terminal 900, but is not limited thereto. The detection apparatus 100 may be a stand-alone computer such as a personal computer or may be a portable computer such as a smartphone, tablet, or notebook computer.

The communication unit 110 controls communication with other computers and so forth such as the user terminal 900 irrespective of whether the communication system is a wired system or a wireless system. The communication unit 110 is a communication interface or the like of the network interface card (NIC) or the like, for example.

The storing unit 120 stores a program executed by the control unit 130, various kinds of data, and so forth, for example. Furthermore, the storing unit 120 includes a knowledge base 121, a class storage part 122, the disease name master data 123, and patient master data 124. The storing unit 120 corresponds to semiconductor memory elements such as random access memory (RAM), read only memory (ROM), and flash memory and a storing apparatus such as a hard disk drive (HDD).

The knowledge base 121 stores various kinds of information such as combinations of a diagnostic condition included in a medical care guideline and prescription medicine, coping method, and so forth. The knowledge base 121 stores a combination of a diagnostic condition such as "the disease name is cerebral infarction and the SBP value is 200 or larger" and prescription medicine and coping method corresponding to the diagnostic condition. To the knowledge base 121, information received from the user terminal 900 or an external database or the like through the communication unit 110 is input in advance, for example.

The class storage part 122 stores information relating to classes processed by an inferring unit 134 and so forth to be described later. The class storage part 122 stores information relating to the subject class 1111 illustrated in FIG. 1, information relating to the input class 2200 illustrated in FIG. 2A, and information relating to the negation class 4111 illustrated in FIG. 3A, for example. The information stored in the class storage part 122 is input by a class generating unit 132 to be described later, for example.

In addition, the class storage part 122 further stores a class list that is information relating to the halfway progress of processing by the inferring unit 134. FIG. 5 is a diagram illustrating one example of a class list in embodiment 1. As illustrated in FIG. 5, the class storage part 122 stores "inference target class list," "excluded class list," and "uncertain basic class list," for example, as information relating to the class. The contents of the class list are registered or updated by a target class identifying unit 133 or a lower-level class extracting unit 135 to be described later.

In FIG. 5, the "inference target class list" stores a list of the class deemed as the target of later inference processing with use of the input class by the inferring unit 134. The "excluded class list" stores a list of the class excluded from the target of inference processing by the inferring unit 134. For example, the excluded classes are the relevant class and the class that contradicts the relevant class and lower-level classes of these classes when it is determined that an input class corresponds to a subject class or a negation class. The "uncertain basic class list" stores a list of the basic class with which an input class is determined as "non-corresponding" by the inferring unit 134 and that is included in a subject class or a negation class.

In the example illustrated in FIG. 5, that the class regarding which the inferring unit 134 executes inference processing with use of an input class next is "¬ C and ¬ D" and that inference processing is not executed regarding "A or B" and "¬ A and ¬ B" are stored. Furthermore, in the example illustrated in ¬ FIG. 5, that the respective basic classes of "C" and "D" are identified as "non-corresponding" is stored.

Figure 6:
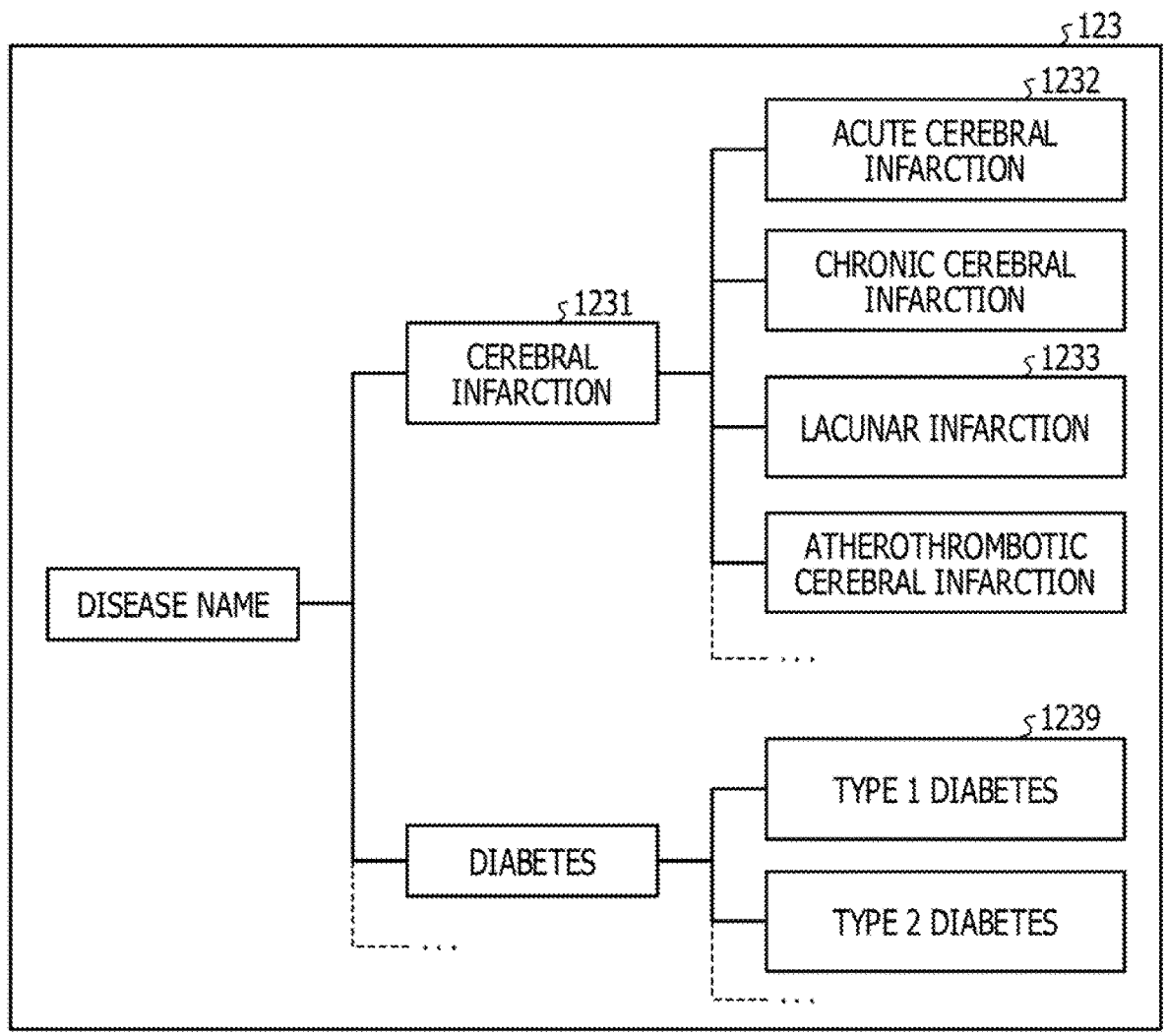
FIG. 6 illustrates one example of disease name master data in embodiment 1.

Referring back to FIG. 4, the disease name master data 123 stores information relating to the hierarchical relationship of the disease name. FIG. 6 is a diagram illustrating one example of disease name master data in embodiment 1. As illustrated in FIG. 6, the disease name master data 123 stores a "cerebral infarction" class 1231, a "diabetes" class, and other classes as lower-level classes of a "disease name" class, for example. Furthermore, the disease name master data 123 illustrated in FIG. 6 stores an "acute cerebral infarction" class 1232, a "chronic cerebral infarction" class, a "lacunar infarction" class 1233, an "atherothrombotic cerebral Infarction" class, and other classes as lower-level classes of the "cerebral Infarction" class 1231, for example.

For example, if an input class includes "disease name: lacunar infarction," the inferring unit 134 refers to the disease name master data 123 illustrated in FIG. 4 and determines that the input class corresponds to the "cerebral infarction" class 1231, which is the higher-level class of the "lacunar infarction" class 1233. Furthermore, if an input class includes "disease name: type 1 diabetes," the inferring unit 134 determines that the input class is "non-corresponding" to the "cerebral infarction" class 1231 because a "type 1 diabetes" class 1239 is not a lower-level class of the "cerebral infarction" class 1231.

Referring back to FIG. 4, the patient master data 124 stores information relating to the patient. FIG. 7 is a diagram illustrating one example of patient master data in embodiment 1. As illustrated in FIG. 7, the patient master data 124 stores the respective items of "age" and "sex," "disease name 1" and "disease name 2," and "SBP value" and "numbness" and "dizziness," for example, with each item associated with a "patient ID." In the present embodiment, the patient master data 124 stores one record per one patient. To the patient master data 124, Information received from the user terminal 900 or an external database or the like through the communication unit 110 is input in advance for example.

In FIG. 7, "patient ID" stores an identifier to uniquely identify the patient. "Disease name 1" and "disease name 2" store the disease names that have become clear regarding the relevant patient. "SBP value" stores the test result of the SBP value of the relevant patient. "Numbness" and "dizziness" store symptoms that have been confirmed about the relevant patient. The number of disease names and the kinds of test result and symptoms are one example and a configuration in which the patient master data 124 stores another test result or symptom or stores three or more disease names may be employed.

Referring back to FIG. 4, the control unit 130 is a processing unit responsible for overall processing of the detection apparatus 100. For example, the control unit 130 is implemented through execution of a program stored in an internal storing apparatus by a central processing unit (CPU), a micro processing unit (MPU), or the like with use of a RAM as a work area. Furthermore, the control unit 130 may be implemented by an integrated circuit such as an application specific integrated circuit (ASIC) or a field programmable gate array (FPGA).

The control unit 130 includes an accepting unit 131, the class generating unit 132, the target class identifying unit 133, the inferring unit 134, the lower-level class extracting unit 135, and an output unit 136. The accepting unit 131, the class generating unit 132, the target class identifying unit 133, the inferring unit 134, the lower-level class extracting unit 135, and the output unit 136 are one example of an electronic circuit possessed by a processor or one example of a process executed by the processor.

Figure 8:
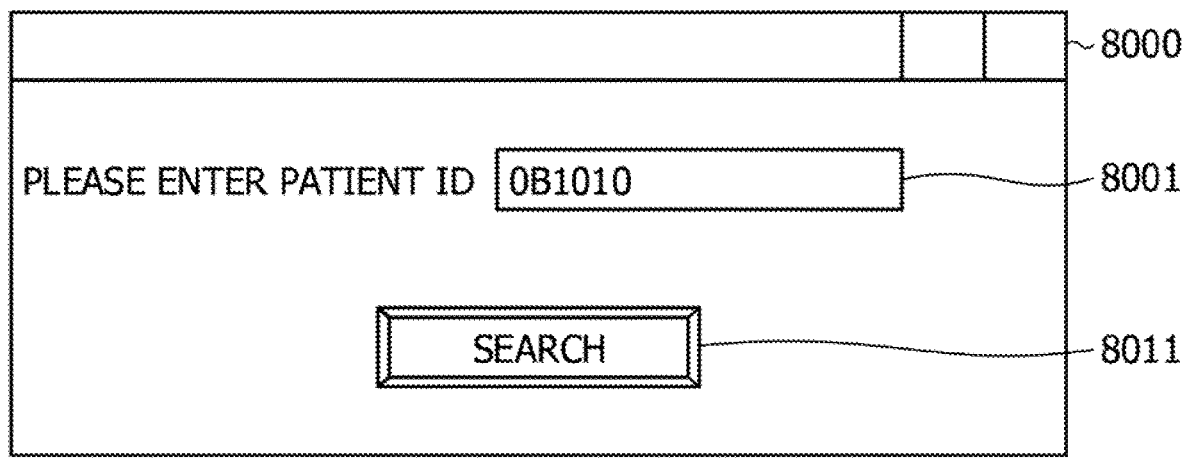
FIG. 8 illustrates one example of a patient selection screen in embodiment 1.

The accepting unit 131 accepts various kinds of requests and input from the user terminal 900 and so forth through the communication unit 110. The accepting unit 131 accepts entry of patient information from the user terminal 900 by causing the user terminal 900 to display a screen like one illustrated in FIG. 8, for example, through the communication unit 110. FIG. 8 is a diagram illustrating one example of a patient selection screen in embodiment 1. A patient selection screen 8000 illustrated in FIG. 8 includes an area 8001 that accepts entry of the patient ID and a search button 8011.

When receiving a patient ID entered in the user terminal 900 through the communication unit 110, the accepting unit 131 refers the patient master data 124 and acquires information relating to the patient corresponding to the patient ID. Then, the accepting unit 131 generates an input class from the acquired information and outputs the input class to the class generating unit 132 and the inferring unit 134.

The accepting unit 131 generates "age: 55," "sex: female," "disease name: lacunar infarction, hypertension" as the input class of the patient corresponding to an entered patient ID "0B1010," for example. On the other hand, the accepting unit 131 does not have to cause "SBP value," "numbness," and "dizziness," which are "unknown," to be included in the input class or may generate an input class indicating that the respective items are "unknown."

Furthermore, the accepting unit 131 accepts, from the user terminal 900, input or selection of information for determining whether or not the input class corresponds to a diagnostic condition, to be described later. The accepting unit 131 updates the input class by using the accepted information for determining whether or not the input class corresponds to a diagnostic condition and outputs the input class after the update to the inferring unit 134.

Referring back to FIG. 4, the class generating unit 132 generates a subject class and a negation class of the subject class based on the input class acquired from the accepting unit 131. The class generating unit 132 generates the subject class by reading out a diagnostic condition stored in the knowledge base 121 and identifying the basic classes included in the diagnostic condition to carry out a logical connection of the basic classes. Furthermore, the class generating unit 132 generates the negation class of the subject class by carrying out a logical connection of classes that contradict the respective basic classes included in the generated subject class. The class generating unit 132 outputs the generated subject class and negation class to the target class identifying unit 133.

Figure 9A:
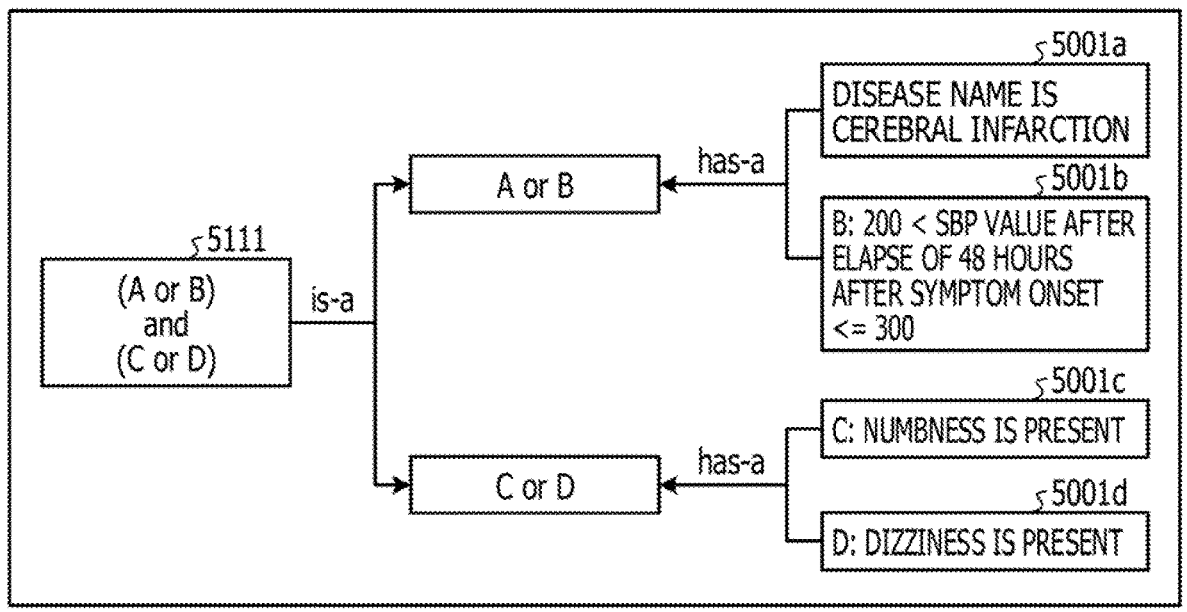
FIG. 9A illustrates one example of a subject class in embodiment 1.

FIG. 9A is a diagram illustrating one example of a subject class in embodiment 1. FIG. 9A illustrates a subject class generated by the class generating unit 132 from a diagnostic condition of "the disease name is cerebral infarction or the SBP value after the elapse of 48 hours after symptom onset surpasses 200 and is 300 or smaller, and numbness or dizziness is present," for example. As illustrated in FIG. 9A, the class generating unit 132 generates, from this diagnostic condition, the respective basic classes 5001a to 5001d of "A: disease name is cerebral infarction," "B: 200<SBP value after the elapse of 48 hours after symptom onset<=300," "C: numbness is present," and "D: dizziness is present."

Furthermore, the class generating unit 132 generates a subject class 5111 of "(A or B) and (C or D)" by carrying out a logical connection of the respective basic classes 5001a to 5001d. For example, the respective basic classes 5001a to 5001d are lower-level classes of the subject class 5111. "(A or B)" is a lower-level class of the subject class 5111 and is the higher-level class of basic class A 5001a and basic class B 5001b. Similarly, "(C or D)" is a lower-level class of the subject class 5111 and is the higher-level class of basic class C 5001c and basic class D 5001d. Each lower-level class of the subject class 5111 is one example of a specific class and the highest-level class of the subject class 5111 is one example of the highest-level class in the hierarchical structure of the subject class.

Figure 9B:
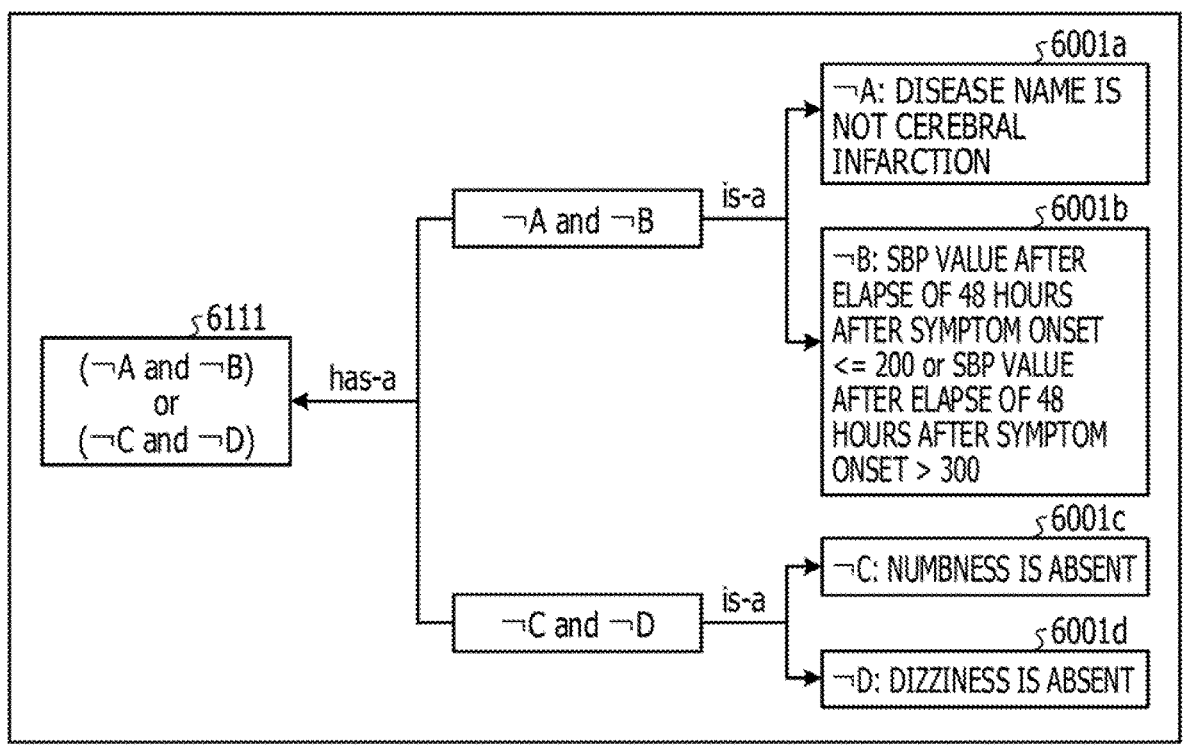
FIG. 9B illustrates one example of a negation class of a subject class in embodiment 1.

Furthermore, the class generating unit 132 generates a negation class 6111 of the subject class 5111 like one illustrated in FIG. 9B. FIG. 9B is a diagram illustrating one example of a negation class of a subject class in embodiment 1. As illustrated in FIG. 9B, the class generating unit 132 generates basic classes 6001a to 6001d that contradict the respective basic classes 5001a to 5001d. For example, the basic class 6001b that contradicts the basic class 5001b is "¬ B: SBP value after the elapse of 48 hours after symptom onset<=200 or SBP value after the elapse of 48 hours after symptom onset>300."

Then the class generating unit 132 generates the negation class 6111 of "(¬ A and ¬ B) or (¬ C and ¬ D)" by carrying out a logical connection of the respective basic classes 6001a to 6001d. "(¬ A and ¬ B)" is a lower-level class of the negation class 6111 and is the higher-level class of basic class "¬ A" 6001a and basic class "¬ B" 6001b. Similarly, "(¬ C and ¬ D)" is a lower-level class of the negation class 6111 and is the higher-level class of basic class "¬ C" 6001c and basic class "¬ D" 6001d. Furthermore, "(¬ A and ¬ B)" is one example of the class corresponding to the specific class "A or B" in the subject class 5111 and "(¬ C and ¬ D)" is one example of the class corresponding to the specific class "C or D" in the subject class 5111.

Referring back to FIG. 4, the target class identifying unit 133 identifies the class to become the target of inference by the inferring unit 134. The target class identifying unit 133 receives output of the subject class and the negation class from the class generating unit 132 and adds the respective classes to the inference target class list. For example, when receiving output of the subject class 5111 and the negation class 6111, the target class identifying unit 133 adds "(A or B) and (C or D)" and "(¬ A and ¬ B) or (¬ C and ¬ D)" to the inference target class list.

Next, the target class identifying unit 133 acquires an inference result from the inferring unit 134 and updates the inference target class list. When acquiring an inference result that the input class corresponds to the class in the inference target class list from the inferring unit 134, the target class identifying unit 133 deletes the relevant class from the inference target class list and adds the relevant class to the excluded class list.

On the other hand, when acquiring an inference result that the input class is "non-corresponding" to the class in the inference target class list from the inferring unit 134, the target class identifying unit 133 outputs the relevant class to the lower-level class extracting unit 135.

When receiving output of lower-level classes of the relevant class from the lower-level class extracting unit 135, the target class identifying unit 133 deletes the relevant class from the inference target class list and adds the output lower-level classes to the inference target class list. On the other hand, when receiving output of information indicating that the relevant class is a basic class from the lower-level class extracting unit 135, the target class identifying unit 133 deletes the relevant class from the inference target class list and adds the relevant class to the uncertain basic class list.

The inferring unit 134 executes detection processing of determining whether or not the input class acquired from the class generating unit 132 corresponds to the respective classes added to the inference target class list. The inferring unit 134 acquires an input class of "age: 55," "sex: female," "disease name: lacunar infarction, hypertension," for example, from the accepting unit 131 and determines whether or not the input class corresponds to the subject class 5111 or the negation class 6111 added to the inference target class list.

The inferring unit 134 outputs the result of the determination of whether or not the input class corresponds to the respective classes added to the inference target class list to the target class identifying unit 133 and the output unit 136. Then, the inferring unit 134 repeats the processing until all classes are deleted from the inference target class list by the target class identifying unit 133.

Furthermore, when receiving output of the input class updated by using the information for determining whether or not the input class corresponds to a diagnostic condition from the accepting unit 131, the inferring unit 134 repeats the processing by using the updated input class.

If determining that the input class is "corresponding" to the highest-level class of the subject class or the negation class, the inferring unit 134 ends the inference processing and outputs the processing result to the output unit 136.

The lower-level class extracting unit 135 refers to the class storage part 122 and identifies lower-level classes of the class output from the target class identifying unit 133. When receiving output of e.g. the class "(A or B) and (C or D)" illustrated in FIG. 9A from the target class identifying unit 133, the lower-level class extracting unit 135 identifies lower-level classes "A or B" and "C or D" of this class.

On the other hand, if determining that a lower-level class does not exist in the relevant class, for example, the relevant class corresponds to a basic class, the lower-level class extracting unit 135 outputs information indicating that the relevant class is a basic class to the target class identifying unit 133. For example, when receiving output of class "A" from the target class identifying unit 133, the lower-level class extracting unit 135 outputs information indicating that class "A" is a basic class.

The output unit 136 outputs the inference result by the inferring unit 134 to the user terminal 900 through the communication unit 110, for example. For example, the output unit 136 refers to the class storage part 122 and waits until all classes are deleted from the inference target class list. If determining that all classes have been deleted from the inference target class list, the output unit 136 outputs the inference result by the inferring unit 134 and the class added to the uncertain basic class list of the class storage part 122.

Furthermore, when receiving output of the processing result of determining that the input class is "corresponding" to the highest-level class of the subject class or the negation class from the inferring unit 134, the output unit 136 outputs a case identification screen 8200 to be described later to the user terminal 900 through the communication unit 110.

Figure 10:
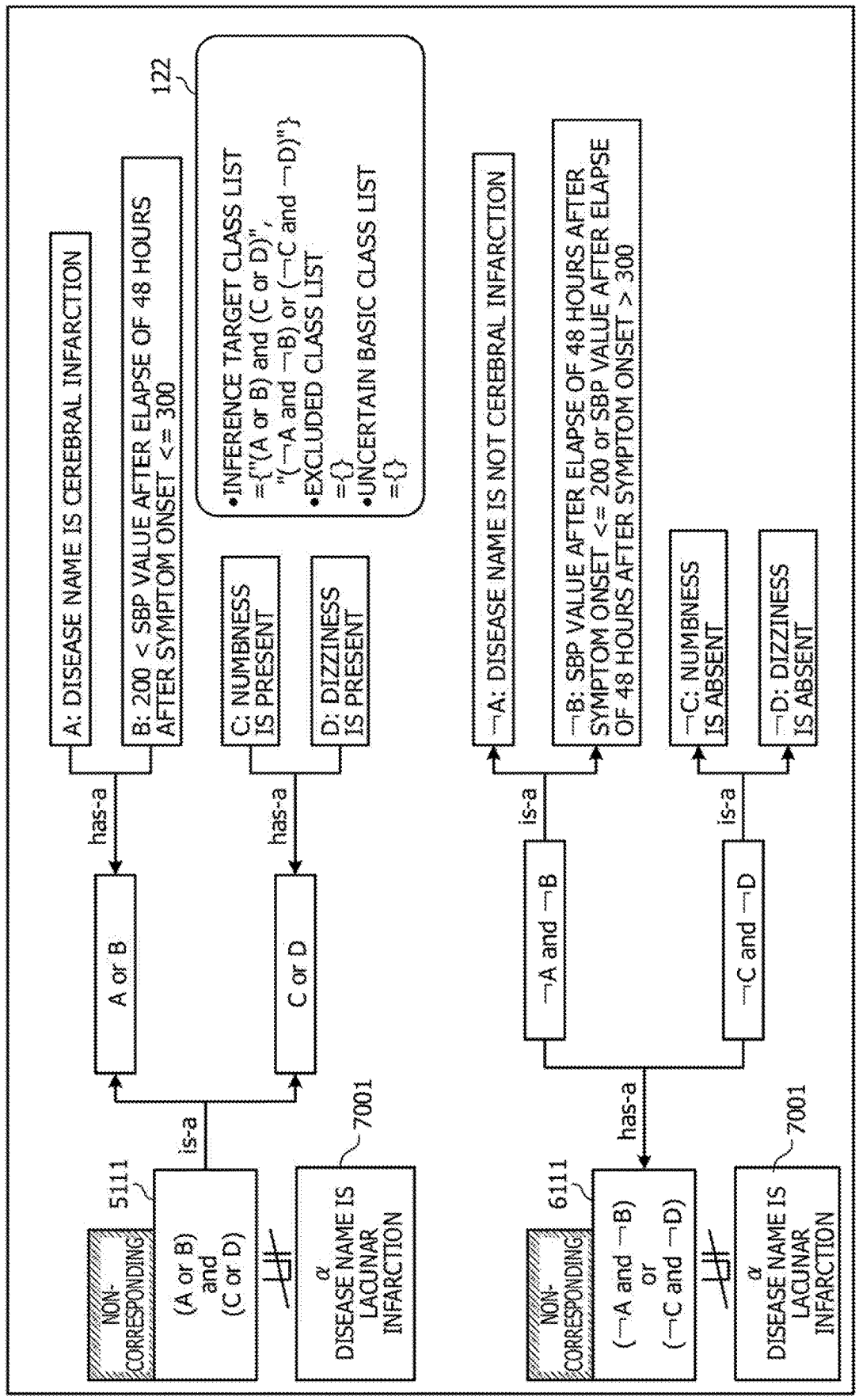
FIG. 10 illustrates one example of halfway progress of detection processing in embodiment 1.

Next, processing by the detection apparatus 100 will be described by using FIG. 10 to FIG. 14. FIG. 10 is a diagram illustrating one example of halfway progress of detection processing in embodiment 1. First, the accepting unit 131 acquires information to identify the patient from the user terminal 900 and generates an input class corresponding to the patient to output the input class to the class generating unit 132 and the inferring unit 134. In the following, the case in which the accepting unit 131 generates an input class 7001 of "disease name is lacunar infarction" will be described.

The class generating unit 132 generates the subject class 5111 like that illustrated in FIG. 9A and the negation class 6111 of the subject class like that illustrated in FIG. 9B and outputs the subject class 5111 and the negation class 6111 to the target class identifying unit 133. As illustrated in FIG. 10, the target class identifying unit 133 adds the subject class 5111 and the negation class 6111 to the inference target class list of the class storage part 122.

Next, the inferring unit 134 infers whether or not the input class 7001 output from the accepting unit 131 corresponds to the subject class 5111 or the negation class 6111 added to the inference target class list.

In this case, the inferring unit 134 determines that the input class 7001 is "non-corresponding" regarding both the subject class 5111 and the negation class 6111 added to the inference target class list, and outputs the inference result to the target class identifying unit 133. For example, the input class 7001 is "non-corresponding" to the subject class 5111 because "C or D" does not correspond. Furthermore, the input class 7001 corresponds to neither "($\neg$ A and $\neg$ B)" nor "($\neg$ C and $\neg$ D)" and therefore is "non-corresponding" also to the negation class 6111. In the present embodiment, information indicating which part of a respective one of the classes does not correspond is not output at the present stage.

When accepting the inference result that the input class 7001 is "non-corresponding," the target class identifying unit 133 outputs the subject class 5111 and the negation class 6111 added to the inference target class list to the lower-level class extracting unit 135.

The lower-level class extracting unit 135 identifies each of lower-level classes of the subject class 5111 and lower-level classes of the negation class 6111. In FIG. 10, the lower-level class extracting unit 135 identifies "A or B" and "C or D" and "($\neg$ A and $\neg$ B)" and "($\neg$ C and $\neg$ D)" and outputs these classes to the target class identifying unit 133.

Figure 11:
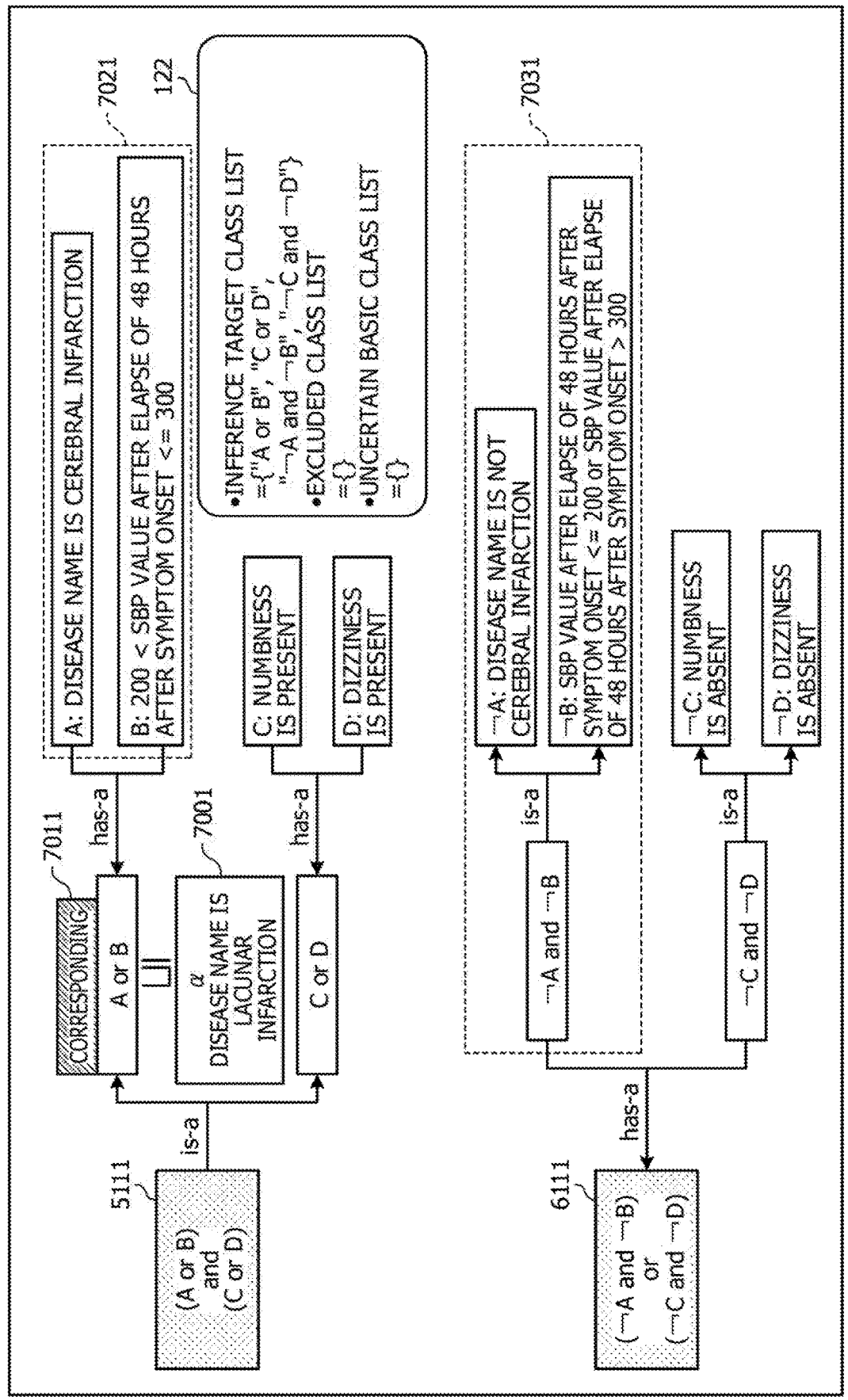
FIG. 11 illustrates another example of halfway progress of detection processing in embodiment 1.

When receiving output of the lower-level classes, as illustrated in FIG. 11, the target class identifying unit 133 deletes the subject class 5111 and the negation class 6111 added to the inference target class list of the class storage part 122 and adds the respective lower-level classes to the inference target class list.

FIG. 11 is a diagram illustrating another example of halfway progress of detection processing in embodiment 1. As illustrated in FIG. 11, to the class storage part 122, "A or B" and "C or D" and "($\neg$ A and $\neg$ B)" and "($\neg$ C and $\neg$ D)," which are the identified lower-level classes, are added as the inference target class list. Then, the inferring unit 134 repeats processing regarding the respective classes added to the inference target class list. For example, the inferring unit 134 determines whether or not the input class 7001 corresponds to the respective classes.

In this case, as represented by numeral 7011, the inferring unit 134 determines that the input class 7011 corresponds to the class "A or B" and outputs the inference result to the target class identifying unit 133. This is because "lacunar infarction" of the input class 7001 is one example of "cerebral Infarction" and therefore it turns out that the input class 7001 corresponds to the class "A or B" irrespective of whether or not the input class 7001 corresponds to basic class B.

Figure 12:
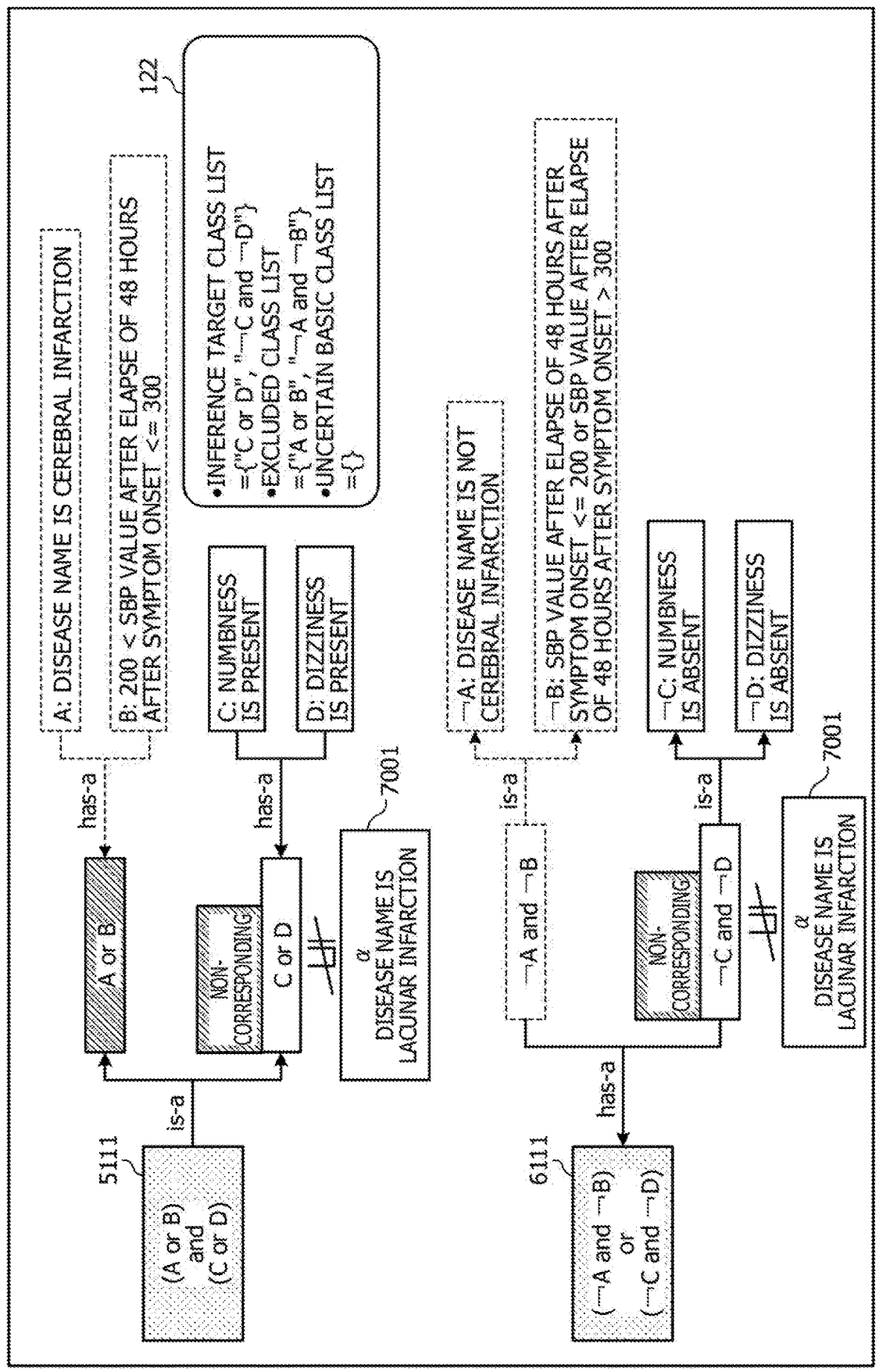
FIG. 12 illustrates another example of halfway progress of detection processing in embodiment 1.

As illustrated in FIG. 12, the target class identifying unit 133 that has received the inference result deletes the class "A or B" from the inference target class list of the class storage part 122 and adds the class "A or B" to the excluded class list. Furthermore, also regarding the contradicting class "($\neg$ A and $\neg$ B)" corresponding to the class "A or B," the target class identifying unit 133 deletes the class from the inference target class list of the class storage part 122 and adds the class to the excluded class list similarly. This is because, when it turns out that the input class corresponds to one class, it turns out that the input class does not correspond to the other class contradicting the one class. Due to this, the respective classes represented by numerals 7021 and 7031 in FIG. 11 are excluded from the target of processing by the inferring unit 134.

FIG. 12 is a diagram illustrating another example of halfway progress of detection processing in embodiment 1. The inferring unit 134 does not repeat processing regarding the respective classes added to the excluded class list of the class storage part 122. For example, the inferring unit 134 does not identify lower-level classes of the respective classes added to the excluded class list and execute inference processing. For example, in the example illustrated in FIG. 11, the inferring unit 134 does not execute inference processing regarding lower-level classes "A" and "B" of the class "A or B" and the class "(¬ A and ¬ B)" and lower-level classes "¬ A" and "¬ B" thereof, represented by numerals 7021 and 7031 in FIG. 11.

Next, the inferring unit 134 refers to the inference target class list and determines whether or not the input class 7001 corresponds regarding the respective added classes of "C or D" and "¬ C and ¬ D." In this case, the inferring unit 134 determines that the input class 7001 is "non-corresponding" to both classes, and outputs the inference result to the target class identifying unit 133. This is because the input class 7001 corresponds to none of "C," "D," "¬ C," and "¬ D." In the present embodiment, information indicating which part of a respective one of the classes does not correspond is not output also at the present stage.

When accepting the inference result that the input class 7001 is "non-corresponding," the target class identifying unit 133 outputs the respective classes of "C or D" and "¬ C and ¬ D" added to the inference target class list to the lower-level class extracting unit 135. The lower-level class extracting unit 135 identifies each of lower-level classes of the respective classes of "C or D" and "¬ C and ¬ D." In FIG. 12, the lower-level class extracting unit 135 identifies "C," "D," "¬ C," and "¬ D" and outputs these classes to the target class identifying unit 133.

Figure 13:
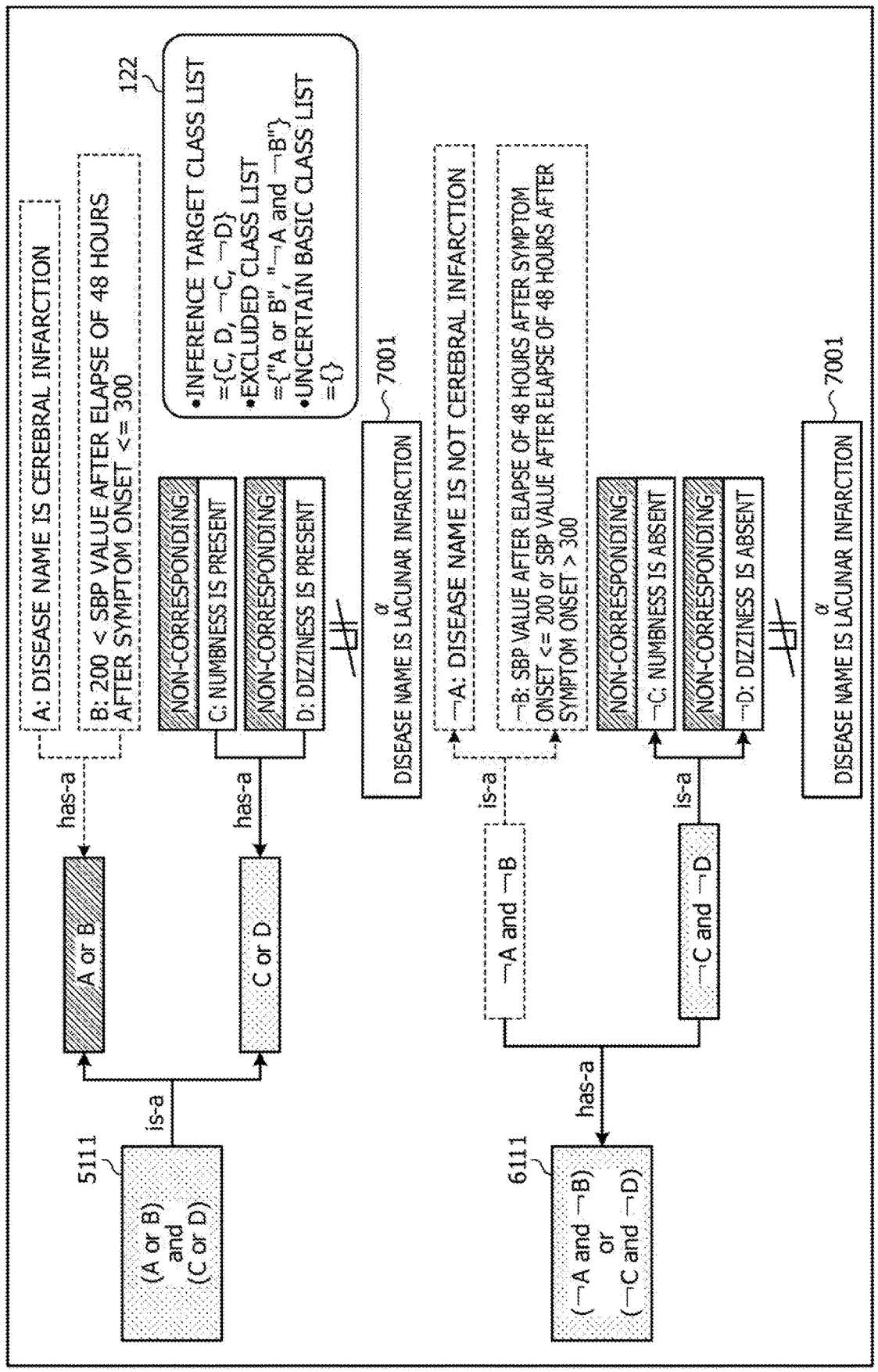
FIG. 13 illustrates another example of halfway progress of detection processing in embodiment 1.

As illustrated in FIG. 13, the target class identifying unit 133 deletes the respective classes of "C or D" and "¬ C and ¬ D" added to the inference target class list of the class storage part 122 and adds the respective output lower-level classes to the inference target class list. FIG. 13 is a diagram illustrating another example of halfway progress of detection processing in embodiment 1. As illustrated in FIG. 13, the output lower-level classes "C," "D," "¬ C," and "¬ D" are added to the inference target class list of the class storage part 122.

Next, the inferring unit 134 refers to the inference target class list and determines whether or not the input class 7001 corresponds also regarding the respective classes of "C," "D," "¬ C," and "¬ D" added to the inference target class list. In this case, the inferring unit 134 determines that the input class 7001 is "non-corresponding" to all classes, and outputs the inference result to the target class identifying unit 133. For example, it turns out that the input class 7001 corresponds to neither basic class C 5001c nor corresponding basic class "¬ C" 6001c. Similarly, it turns out that the input class 7001 corresponds to neither basic class D 5001d nor corresponding basic class "¬ D" 6001d.

When accepting the inference result that the input class 7001 is "non-corresponding," the target class identifying unit 133 outputs the respective classes of "C," "D," "¬ C," and "¬ D" added to the inference target class list to the lower-level class extracting unit 135. In this case, because "C," "D," "¬ C," and "¬ D" are basic classes, the lower-level class extracting unit 135 outputs information indicating that all classes are basic classes to the target class identifying unit 133.

Figure 14:
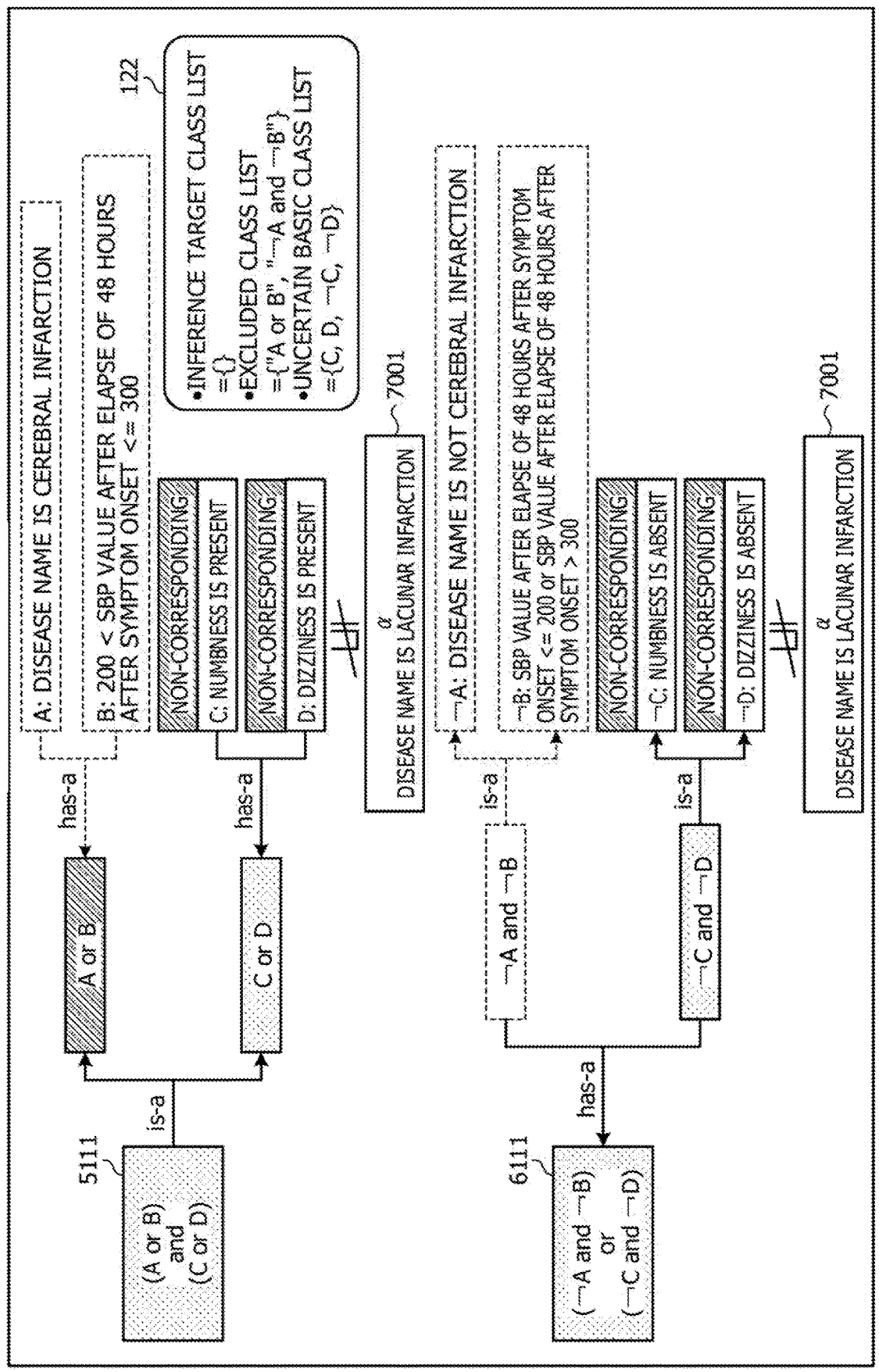
FIG. 14 illustrates one example of result of detection processing in embodiment 1.

As illustrated in FIG. 14, the target class identifying unit 133 deletes the respective classes of "C," "D," "¬ C," and "¬ D" added to the inference target class list of the class storage part 122 and adds these classes to the uncertain basic class list. Then, the output unit 136 outputs the processing result including the classes added to the uncertain basic class list of the class storage part 122 and the inference result acquired from the inferring unit 134 to the user terminal 900 through the communication unit 110.

FIG. 14 is a diagram illustrating one example of result of detection processing in embodiment 1. The output unit 136 outputs, to the user terminal 900, information indicating that the input class 7001 corresponds to the class "A or B" and the respective basic classes of "C," "D," "¬ C," and "¬ D" are uncertain. At this time, the output unit 136 outputs a screen to request entry or selection of the uncertain basic class like one illustrated in FIG. 15. FIG. 15 is a diagram illustrating one example of an inference result screen in embodiment 1.

As illustrated in FIG. 15, an inference result screen 8100 includes an area 8101 that asks for entry or selection of information relating to the uncertain class and an enter button 8111. For example, the area 8101 includes the condition relating to basic class C 5001c and basic class "¬ C" 6001c and the condition relating to basic class D 5001d and basic class "¬ D" 6001d, i.e. information relating to whether "numbness" and "dizziness" are present or absent. By causing the user terminal 900 to display such a screen, the output unit 136 may prompt entry or selection of information for determining whether or not the input class corresponds to the diagnostic condition.

When accepting entry or selection of the information for determining whether or not the input class corresponds to the diagnostic condition from the user terminal 900, the accepting unit 131 updates the input class and outputs the input class to the inferring unit 134. The inferring unit 134 determines that the updated input class accords with the highest-level class of the subject class as the result of repetition of inference processing with use of the updated input class. In this case, the inferring unit 134 outputs, to the output unit 136, the processing result of determining that the input class is "corresponding" to the highest-level class of the subject class or the negation class.

Figure 16:
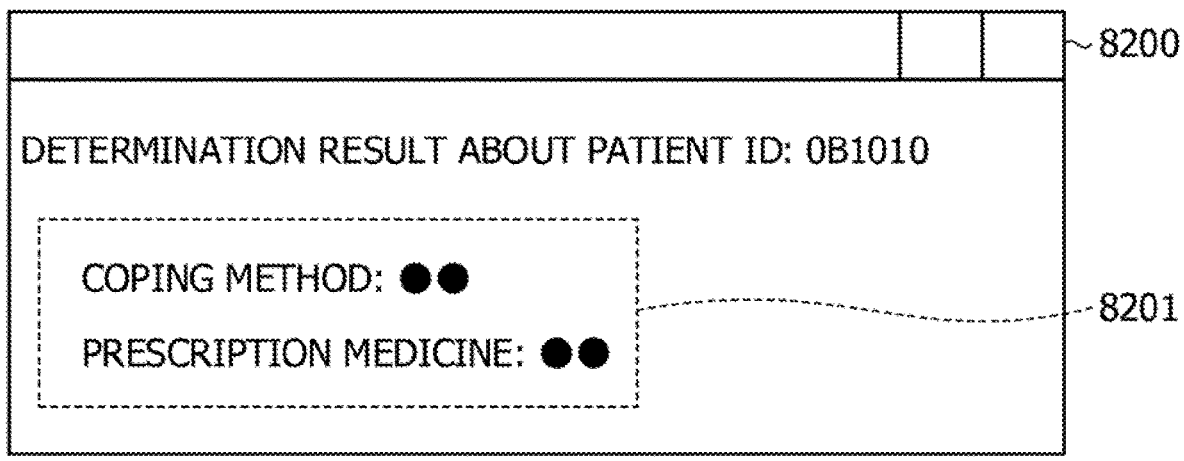
FIG. 16 illustrates one example of a case identification screen in embodiment 1.

The output unit 136 outputs the case identification screen 8200 like that illustrated in FIG. 16 to the user terminal 900 through the communication unit 110. FIG. 16 is a diagram illustrating one example of a case identification screen in embodiment 1. The case identification screen 8200 illustrated in FIG. 16 includes information 8201 indicating coping method, prescription medicine, and so forth that may be inferred due to "corresponding" of the input class to the subject class or the negation class.

[Flow of Processing]

Figure 17A:
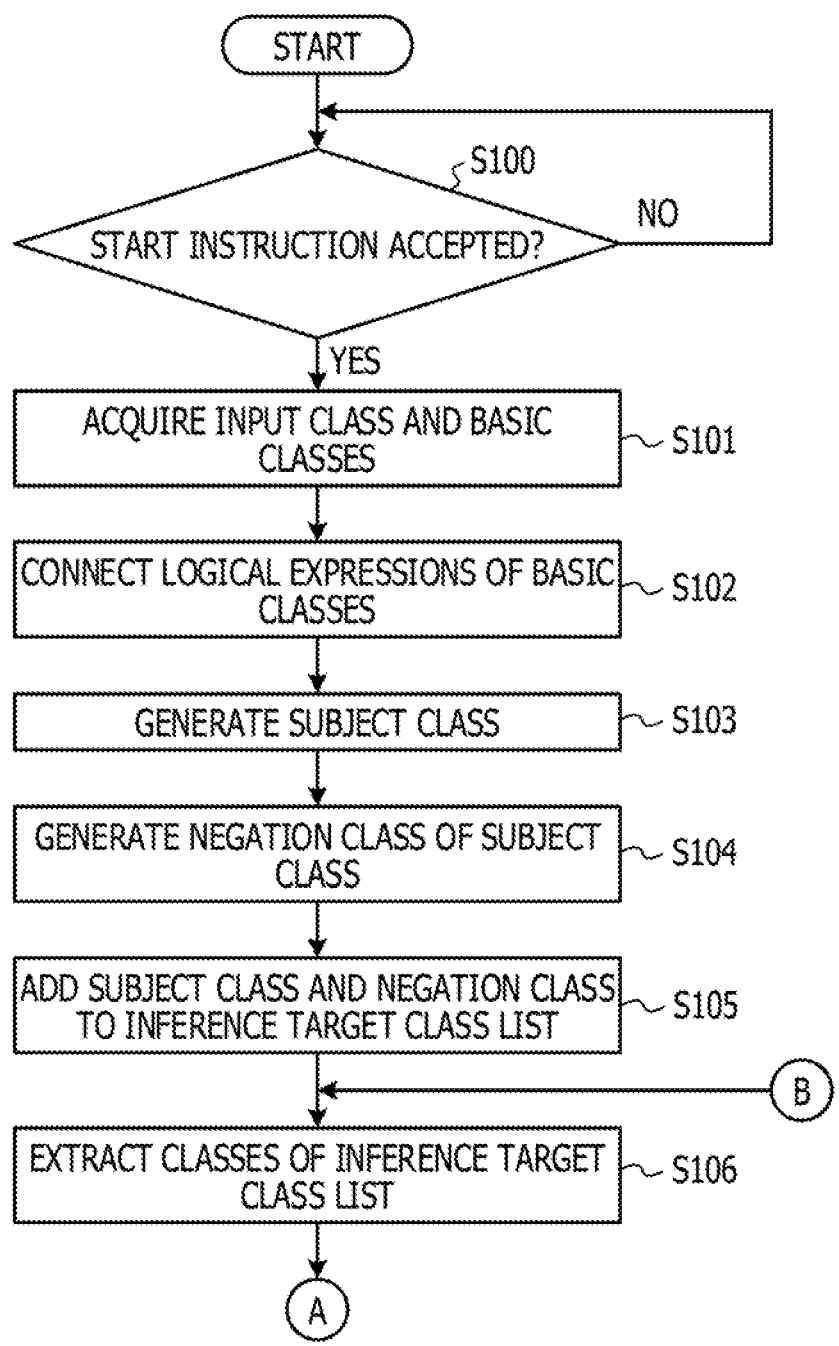
FIGS. 17A and 17B illustrate one example of detection processing in embodiment 1.
Figure 17B:
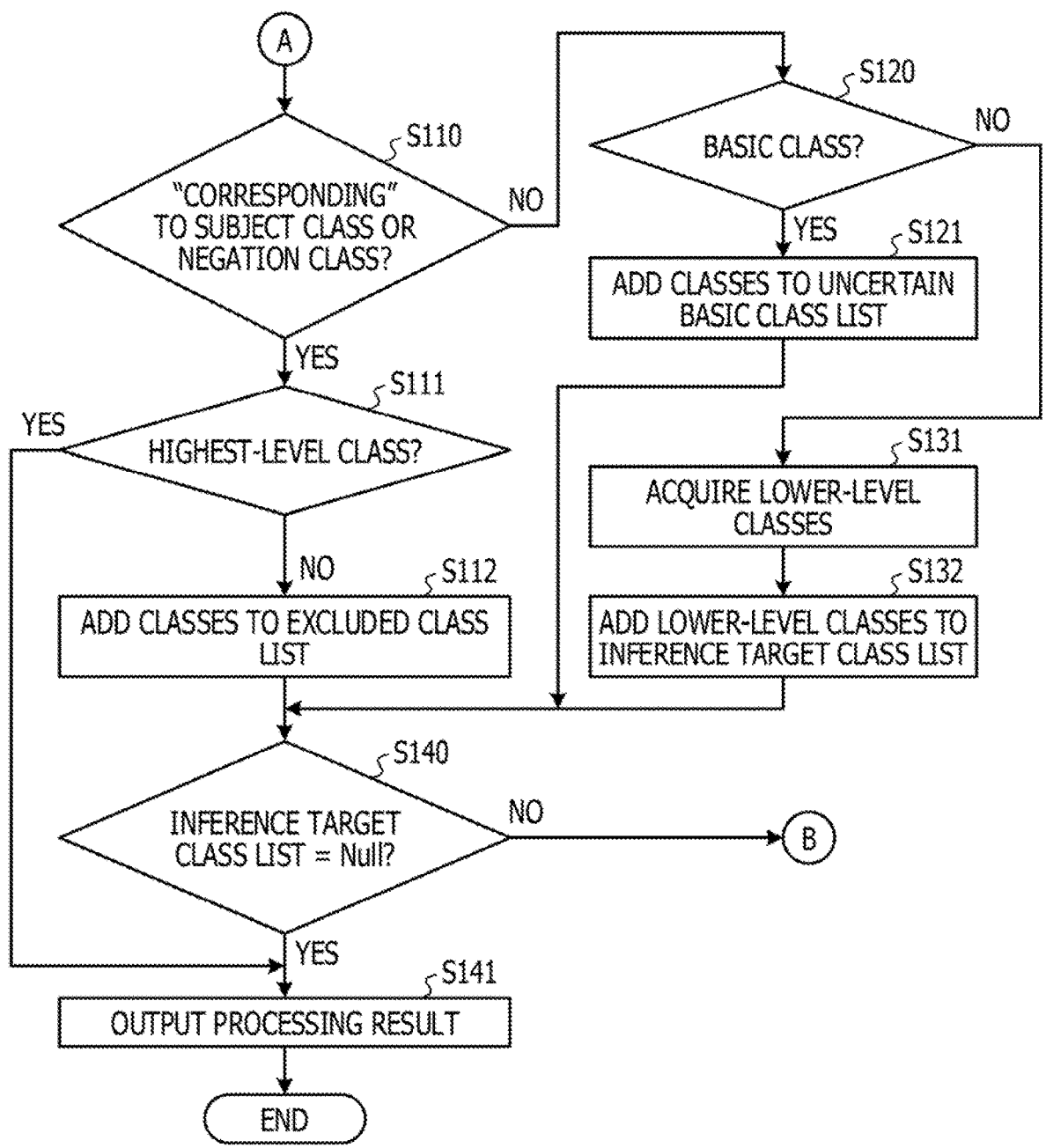

Next, processing in the present embodiment will be described by using FIGS. 17A and 17B. FIG. 17 (i.e. FIGS. 17A and 17B) is a flowchart illustrating one example of detection processing in embodiment 1. As represented in FIG. 17, the accepting unit 131 of the detection apparatus 100 waits until accepting a start instruction including information relating to a patient from the user terminal 900 through the communication unit 110, for example (S100: No).

If determining that a start instruction has been accepted (S100: Yes), the accepting unit 131 outputs the accepted information relating to a patient to the class generating unit 132. The class generating unit 132 that has acquired the information relating to the patient refers to the knowledge base 121 and acquires basic classes. Furthermore, the class generating unit 132 refers to the patient master data 124 and generates an input class corresponding to the information relating to the patient (S101).

Next, the class generating unit 132 connects logical expressions of the acquired basic classes (S102) and generates a subject class (S103). Furthermore, the class generating unit 132 generates a negation class that contradicts the subject class (S104) and outputs the generated subject class and negation class to the target class identifying unit 133.

The target class identifying unit 133 adds the output subject class and negation class to the inference target class list of the class storage part 122 (S105). Next, the inferring unit 134 refers to the class storage part 122 and extracts the subject class and negation class thereof added to the inference target class list (S106). Then, the inferring unit 134 determines whether or not the input class corresponds to the extracted subject class or negation class thereof (S110).

If determining that the input class is "non-corresponding" to the extracted subject class or negation class thereof (S110: No), the inferring unit 134 outputs the inference result to the target class identifying unit 133.

The target class identifying unit 133 determines whether or not the relevant target classes are basic classes (S120). If determining that the relevant target classes are basic classes (S120: Yes), the target class identifying unit 133 adds the relevant target classes to the uncertain basic class list (S121) and makes a transition to S140.

On the other hand, if determining that the relevant subject classes are not basic classes (S120: No), the target class identifying unit 133 acquires lower-level classes from the lower-level class extracting unit 135 (S131). Then, the target class identifying unit 133 adds the acquired lower-level classes to the inference target class list (S132) and makes a transition to S140.

Referring back to S110, if determining that the input class is "corresponding" to the extracted subject class or negation class thereof (S110: Yes), the inferring unit 134 determines whether or not the corresponding class is the highest-level class of the subject class or negation class thereof (S111). If determining that the corresponding class is the highest-level class (S111: Yes), the inferring unit 134 outputs the inference result to the output unit 136. The output unit 136 outputs the processing result to the user terminal 900 (S141) and ends the processing.

On the other hand, if it is determined that the corresponding class is not the highest-level class (S111: No), the target class identifying unit 133 deletes lower-level classes of the corresponding class and the class that contradicts the corresponding class and lower-level classes thereof from the inference target class list. In conjunction with this, the target class identifying unit 133 adds the respective classes deleted from the inference target class list to the excluded class list (S112).

Then, the target class identifying unit 133 determines whether or not the inference target class list is "Null," for example, the classes added to the inference target class list have been all deleted (S140). If it is determined that the inference target class list is not "Null" (S140: No), the inferring unit 134 returns to S106 and repeats the processing. On the other hand, if it is determined that the inference target class list is "Null" (S140: Yes), the output unit 136 outputs the processing result to the user terminal 900 (S141) and ends the processing.

As described above, a detection program in the present embodiment causes a computer to execute processing of determining whether or not an input class corresponds to any of specific classes in individual subject classes of a knowledge base including a hierarchical structure and classes corresponding to specific classes in negation classes that contradict the subject classes. If it is determined that the input class corresponds to none of the specific classes and the corresponding classes, the detection program causes the computer to execute processing of outputting information relating to the determined specific class. This allows refinement detection of the class.

Furthermore, the detection program in the present embodiment may define the subject class based on basic classes each made by defining a single concept under which a lower-level class does not exist and a logical connection and define the negation class based on basic classes and a logical connection that contradicts the logical connection of the subject class. In addition, the processing of outputting by the detection program may output the basic class that is the class about which it is determined that the lower-level class does not exist as an undefined class. This may detect the input class to be identified.

Moreover, if it is determined that the input class corresponds to any of the specific classes and the corresponding classes, lower-level classes of the class determined as corresponding and classes equal to or lower than the contradicting class corresponding to the class determined as corresponding may be excluded from the target of the subsequent processing of inference. This may reduce the number of classes deemed as the target of the inference processing.

Embodiment 2

Although the embodiment of the present disclosure is described thus far, the present disclosure may be carried out in various different modes besides the above-described embodiment. Furthermore, the respective kinds of processing diagrammatically represented are not limited to the above-described order. The respective kinds of processing may be simultaneously executed or be executed with change in the order in a range in which contradiction is not caused in the contents of the processing.

[System]

Furthermore, the respective constituent elements of the respective units that are diagrammatically represented do not necessarily have to be configured as diagrammatically represented physically. For example, concrete forms of distribution and integration of the respective units are not limited to the diagrammatically-represented forms and all or part of the respective units may be configured to be distributed or integrated functionally or physically in an arbitrary unit according to various kinds of loads, the status of use, and so forth. For example, the target class identifying unit 133 and the lower-level class extracting unit 135 may be integrated and the class storage part 122 may be distributed into a storage part of the subject class and the negation class and a storage part of the class lists.

Moreover, all or an arbitrary part of the respective processing functions carried out in the respective apparatuses may be executed on a CPU (or microcomputer such as MPU or micro controller unit (MCU)). Furthermore, it goes without saying that all or an arbitrary part of the respective processing functions may be executed on a program analyzed and executed by a CPU (or microcomputer such as MPU or MCU) or on hardware based on wired logic.

[Detection Program]

Figure 18:
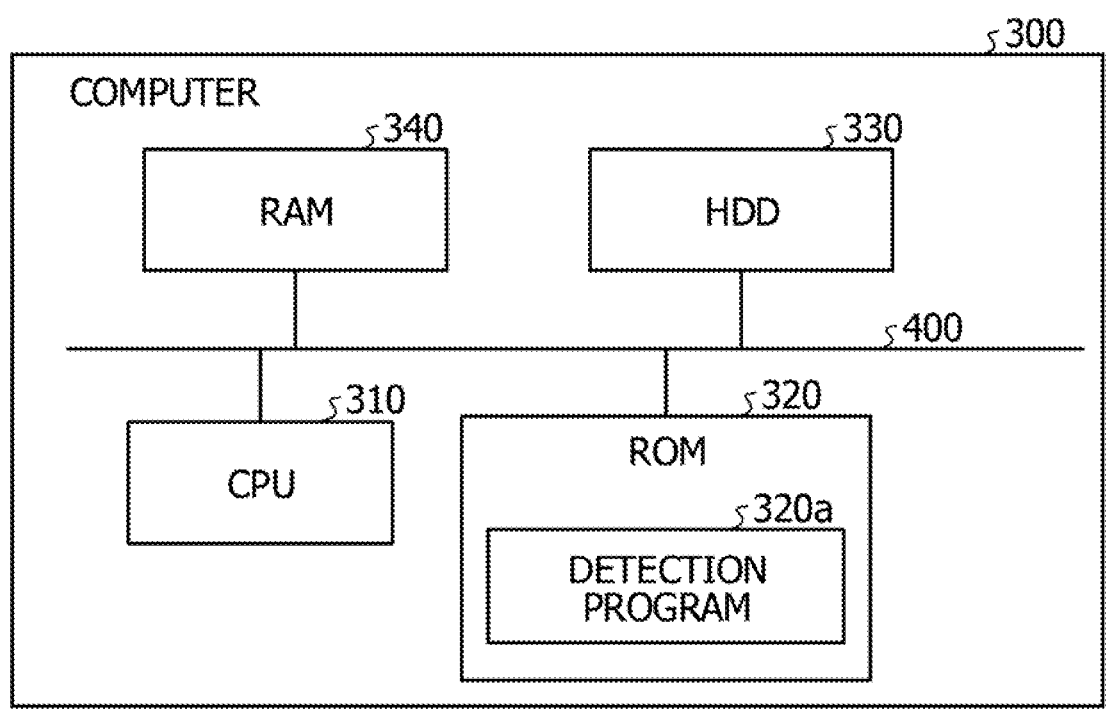
FIG. 18 illustrates one example of a computer that executes a detection program.

Furthermore, it is also possible to implement various kinds of processing described in the above-described embodiment through execution of a program prepared in advance by a computer system such as a personal computer or work station. Thus, in the following, one example of a computer system that executes a program having similar functions to the above-described embodiment will be described. FIG. 18 is a diagram illustrating one example of a computer that executes a detection program.

As illustrated in FIG. 18, a computer 300 includes a CPU 310, a ROM 320, an HDD 330, and a RAM 340. These respective units 310 to 340 are coupled through a bus 400.

A detection program 320*a* that exerts similar functions to the respective processing units of the above-described embodiment 1 is stored in the ROM 320 in advance. For example, the detection program 320*a* that exerts similar functions to the accepting unit 131, the class generating unit 132, the target class identifying unit 133, the inferring unit 134, the lower-level class extracting unit 135, and the output unit 136 of the above-described embodiment 1 is stored. The detection program 320*a* may be split as appropriate.

Furthermore, the CPU 310 carries out similar operation to the respective control units of embodiment 1 by reading out the detection program 320*a* from the ROM 320 and executing the detection program 320*a*. For example, the detection program 320*a* carries out similar operation to the accepting unit 131, the class generating unit 132, the target class identifying unit 133, the inferring unit 134, the lower-level class extracting unit 135, and the output unit 136 of embodiment 1.

The above-described detection program 320*a* does not necessarily have to be stored in the ROM 320 from the beginning. The detection program 320*a* may be stored in the HDD 330.

For example, the program may be stored in "portable physical media" such as flexible disc (FD), compact disc (CD)-ROM, digital versatile disc (DVD) disc, magneto-optical disc, and integrated circuit (IC) card inserted in the computer 300. Then, the computer 300 may read out the program from these media and execute the program.

Moreover, the program may be stored in "other computers (or servers)" coupled to the computer 300 through a public line, the Internet, a local area network (LAN), a wide area network (WAN), and so forth. Then, the computer 300 may read out the program from these computers and execute the program.

All examples and conditional language recited herein of the RFID tag and the high frequency circuit are intended for pedagogical purposes to aid the reader in understanding the invention and the concepts contributed by the inventor to furthering the art, and are to be construed as being without limitation to such specifically recited examples and conditions, nor does the organization of such examples in the specification relate to a showing of the superiority and inferiority of the invention. Although the embodiments of the present invention have been described in detail, it should be understood that the various changes, substitutions, and alterations could be made hereto without departing from the spirit and scope of the invention.

What is claimed is:

1. A detection method comprising:
   executing first processing that includes
     comparing an input class with a first class, the input class including one or more of pairs each including an attribute and an attribute value associated with the attribute, the first class including one or more pieces of first condition information each indicating a condition to be compared with the attribute value of a corresponding attribute from among the one or more of pairs included in the input class, and
     in response to the comparing of the input class and the first class, obtaining a first determination result by determining, for each of the one or more pieces of first condition information included in the first class, whether the condition indicated by the respective first condition information is satisfied by the attribute value of the corresponding attribute from among the one or more of pairs included in the input class;
   executing second processing in response to the first determination result indicating that the condition indicated by at least any one of the one or more pieces of first condition information included in the first class has not been satisfied by the input class, the second processing including
     comparing the input class with a second class, the second class including one or more pieces of second condition information each indicating a condition to be compared with the attribute value of a corresponding attribute from among the one or more of pairs included in the input class, the condition indicated in each of the one or more pieces of second condition information being a condition contradicting the respective condition indicated by the first class, and
     in response to the comparing of the input class and the second class, obtaining a second determination result by determining, for each of the one or more pieces of second condition information included in the second class, whether the condition indicated by the respective second condition information is satisfied by the attribute value of the corresponding attribute from among the one or more of pairs included in the input class; and
   executing third processing that includes
     outputting first information in response to the first determination result indicating that the condition indicated by each of the one or more pieces of first condition information included in the first class has been satisfied by the input class,
     outputting second information in response to the second determination result indicating that the condition indicated by each of the one or more pieces of second condition information included in the second class has been satisfied by the input class, the second information being associated with a status in that at least any one of the one or more of pairs included in the input class has the attribute value contradicting any of the one or more pieces of first condition information included in the first class, and
     outputting third information in response to the second determination result indicating that the condition indicated by any of the one or more pieces of second condition information included in the second class has not been satisfied by the input class, the third information being associated with a status in that at least any one of the one or more of pairs included in the input class has no attribute value.

2. The detection method according to claim 1,
wherein the third processing includes outputting information relating to an attribute value that does not correspond to the conditions included in the negation class among the one or more attribute values included in the input class determined as non-corresponding by the second processing.

3. The detection method according to claim 2, the method further comprising:
executing fourth processing that includes
classifying the input class into a first group when the determination result in the first processing indicates that the input class corresponds to any of the one or more conditions defined in the subject class,
classifying the input class into a second group when the determination result in the second processing indicates that the input class corresponds to any of the one or more second conditions defined in the negation class, and
classifying the input class into a third group when both the determination result in the first processing and the determination result in the second processing indicate that the input class is non-corresponding.

4. The detection method according to claim 1, the method further comprising:
executing fifth processing that includes
reading out a diagnostic condition stored in a knowledge base,
identifying a basic class relating to the diagnostic condition,
when a plurality of basic classes are identified as the relating basic classes, identifying a logical connection that represents a logical combination of the relating basic classes based on the diagnostic condition, and
generating a subject class having the relating basic classes and the logical connection; and
executing sixth processing that includes
identifying second basic classes that contradict the basic classes of the subject class,
identifying a second logical connection that represents a logical combination of the second basic classes based on a condition that contradicts the diagnostic condition, and
generating a negation class having the second basic classes and the second logical connection,
wherein, when any of the one or more attribute values included in the input class corresponds to the basic classes and the logical connection of the subject class, the first processing is configured to determine that the attribute value of the input class corresponds to any of the one or more conditions defined in the subject class,
wherein, when at least any of the one or more attribute values included in the input class corresponds to the second basic classes and the second logical connection of the negation class, the second processing is configured to determine that the attribute value of the input class corresponds to any of the one or more second conditions defined in the negation class.

5. The detection method according to claim 4,
wherein the third processing is configured to output information relating to an attribute value that does not correspond to the second basic classes and the second logical connection included in the negation class among the one or more attribute values included in the input class determined as non-corresponding by the second processing.

6. A detection apparatus comprising:
a memory; and
a processor coupled to the memory and configured to
execute first processing that includes
comparing an input class with a first class, the input class including one or more of pairs each including an attribute and an attribute value associated with the attribute, the first class including one or more pieces of first condition information each indicating a condition to be compared with the attribute value of a corresponding attribute from among the one or more of pairs included in the input class, and
in response to the comparing of the input class and the first class, obtaining a first determination result by determining, for each of the one or more pieces of first condition information included in the first class, whether the condition indicated by the respective first condition information is satisfied by the attribute value of the corresponding attribute from among the one or more of pairs included in the input class;
execute second processing in response to the first determination result indicating that the condition indicated by at least any one of the one or more pieces of first condition information included in the first class has not been satisfied by the input class, the second processing including
comparing the input class with a second class, the second class including one or more pieces of second condition information each indicating a condition to be compared with the attribute value of a corresponding attribute from among the one or more of pairs included in the input class, the condition indicated in each of the one or more pieces of second condition information being a condition contradicting the respective condition indicated by the first class, and
in response to the comparing of the input class and the second class, obtaining a second determination result by determining, for each of the one or more pieces of second condition information included in the second class, whether the condition indicated by the respective second condition information is satisfied by the attribute value of the corresponding attribute from among the one or more of pairs included in the input class; and
execute third processing that includes
outputting first information in response to the first determination result indicating that the condition indicated by each of the one or more pieces of first condition information included in the first class has been satisfied by the input class,
outputting second information in response to the second determination result indicating that the condition indicated by each of the one or more pieces of second condition information included in the second class has been satisfied by the input class, the second information being associated with a status in that at least any one of the one or more of pairs included in the input class has the attribute value contradicting any of the one or more pieces of first condition information included in the first class, and
outputting third information in response to the second determination result indicating that the condition indicated by any of the one or more pieces of second condition information included in the second class has not been satisfied by the input class, the third information being associated with a status in that at least any one of the one or more of pairs included in
the input class has no attribute value.

7. The detection apparatus according to claim 6,
wherein the third processing includes outputting information relating to an attribute value that does not correspond to the conditions included in the negation class among the one or more attribute values included in the input class determined as non-corresponding by the second processing.

8. The detection apparatus according to claim 7,
wherein the processor is further configured to
execute fourth processing that includes
classifying the input class into a first group when the determination result in the first processing indicates that the input class corresponds to any of the one or more conditions defined in the subject class,
classifying the input class into a second group when the determination result in the second processing indicates that the input class corresponds to any of the one or more second conditions defined in the negation class, and
classifying the input class into a third group when both the determination result in the first processing and the determination result in the second processing indicate that the input class is non-corresponding.

9. The detection apparatus according to claim 6,
wherein the processor is further configured to:
execute fifth processing that includes
reading out a diagnostic condition stored in a knowledge base,
identifying a basic class relating to the diagnostic condition,
when a plurality of basic classes are identified as the relating basic classes, identifying a logical connection that represents a logical combination of the relating basic classes based on the diagnostic condition, and
generating a subject class having the relating basic classes and the logical connection; and
execute sixth processing that includes
identifying second basic classes that contradict the basic classes of the subject class,
identifying a second logical connection that represents a logical combination of the second basic classes based on a condition that contradicts the diagnostic condition, and
generating a negation class having the second basic classes and the second logical connection,
wherein, when any of the one or more attribute values included in the input class corresponds to the basic classes and the logical connection of the subject class, the first processing is configured to determine that the attribute value of the input class corresponds to any of the one or more conditions defined in the subject class,
wherein, when at least any of the one or more attribute values included in the input class corresponds to the second basic classes and the second logical connection of the negation class, the second processing is further configured to determine that the attribute value of the input class corresponds to any of the one or more second conditions defined in the negation class.

10. The detection apparatus according to claim 9,
wherein the third processing is configured to output information relating to an attribute value that does not correspond to the second basic classes and the second logical connection included in the negation class among the one or more attribute values included in the input class determined as non-corresponding by the second processing.

11. A non-transitory computer-readable storage medium for storing a detection program that causes a computer to execute a process, the process comprising:
executing first processing that includes
comparing an input class with a first class, the input class including one or more of pairs each including an attribute and an attribute value associated with the attribute, the first class including one or more pieces of first condition information each indicating a condition to be compared with the attribute value of a corresponding attribute from among the one or more of pairs included in the input class, and
in response to the comparing of the input class and the first class, obtaining a first determination result by determining, for each of the one or more pieces of first condition information included in the first class, whether the condition indicated by the respective first condition information is satisfied by the attribute value of the corresponding attribute from among the one or more of pairs included in the input class;
executing second processing in response to the first determination result indicating that the condition indicated by at least any one of the one or more pieces of first condition information included in the first class has not been satisfied by the input class, the second processing including
comparing the input class with a second class, the second class including one or more pieces of second condition information each indicating a condition to be compared with the attribute value of a corresponding attribute from among the one or more of pairs included in the input class, the condition indicated in each of the one or more pieces of second condition information being a condition contradicting the respective condition indicated by the first class, and
in response to the comparing of the input class and the second class, obtaining a second determination result by determining, for each of the one or more pieces of second condition information included in the second class, whether the condition indicated by the respective second condition information is satisfied by the attribute value of the corresponding attribute from among the one or more of pairs included in the input class; and
executing third processing that includes
outputting first information in response to the first determination result indicating that the condition indicated by each of the one or more pieces of first condition information included in the first class has been satisfied by the input class,
outputting second information in response to the second determination result indicating that the condition indicated by each of the one or more pieces of second condition information included in the second class has been satisfied by the input class, the second information being associated with a status in that at least any one of the one or more of pairs included in the input class has the attribute value contradicting any of the one or more pieces of first condition information included in the first class, and
outputting third information in response to the second determination result indicating that the condition indicated by any of the one or more pieces of second condition information included in the second class has not been satisfied by the input class, the third information being associated with a status in that at least any one of the one or more of pairs included in the input class has no attribute value.

12. The non-transitory computer-readable storage medium according to claim 11,
wherein the third processing includes outputting information relating to an attribute value that does not correspond to the conditions included in the negation class among the one or more attribute values included in the input class determined as non-corresponding by the second processing.

13. The non-transitory computer-readable storage medium according to claim 12, the process further comprising:
executing fourth processing that includes
classifying the input class into a first group when the determination result in the first processing indicates that the input class corresponds to any of the one or more conditions defined in the subject class,
classifying the input class into a second group when the determination result in the second processing indicates that the input class corresponds to any of the one or more second conditions defined in the negation class, and
classifying the input class into a third group when both the determination result in the first processing and the determination result in the second processing indicate that the input class is non-corresponding.

14. The non-transitory computer-readable storage medium according to claim 11, the process further comprising:
executing fifth processing that includes
reading out a diagnostic condition stored in a knowledge base,
identifying a basic class relating to the diagnostic condition,
when a plurality of basic classes are identified as the relating basic classes, identifying a logical connection that represents a logical combination of the relating basic classes based on the diagnostic condition, and
generating a subject class having the relating basic classes and the logical connection; and
executing sixth processing that includes
identifying second basic classes that contradict the basic classes of the subject class,
identifying a second logical connection that represents a logical combination of the second basic classes based on a condition that contradicts the diagnostic condition, and
generating a negation class having the second basic classes and the second logical connection,
wherein, when any of the one or more attribute values included in the input class corresponds to the basic classes and the logical connection of the subject class, the first processing is configured to determine that the attribute value of the input class corresponds to any of the one or more conditions defined in the subject class,
wherein, when at least any of the one or more attribute values included in the input class corresponds to the second basic classes and the second logical connection of the negation class, the second processing is configured to determine that the attribute value of the input class corresponds to any of the one or more second conditions defined in the negation class.

15. The non-transitory computer-readable storage medium according to claim 14,
wherein the third processing is configured to output information relating to an attribute value that does not correspond to the second basic classes and the second logical connection included in the negation class among the one or more attribute values included in the input class determined as non-corresponding by the second processing.

* * * * *